(12) United States Patent  
Yamaguchi et al.

(10) Patent No.: US 8,358,821 B2  
(45) Date of Patent: Jan. 22, 2013

(54) IMAGE PROCESSING SYSTEM, IMAGE PROCESSING METHOD, AND COMPUTER READABLE MEDIUM

(75) Inventors: Hiroshi Yamaguchi, Kanagawa (JP); Shinichi Shimotsu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1074 days.

(21) Appl. No.: 12/314,202

(22) Filed: Dec. 5, 2008

(65) Prior Publication Data

US 2009/0147998 A1 Jun. 11, 2009

(30) Foreign Application Priority Data

Dec. 5, 2007 (JP) ................................. 2007-314496

(51) Int. Cl.  
*G06K 9/00* (2006.01)
(52) U.S. Cl. ...................................................... 382/128
(58) Field of Classification Search .................. 382/106, 382/128, 154; 600/424, 473, 476, 478; 356/432  
See application file for complete search history.

(56) References Cited

U.S. PATENT DOCUMENTS

| | | | |
|---|---|---|---|
| 5,879,284 A | 3/1999 | Tsujita | 600/109 |
| 6,230,046 B1* | 5/2001 | Crane et al. | 600/476 |
| 2003/0002028 A1* | 1/2003 | Rice et al. | 356/39 |
| 2004/0015062 A1* | 1/2004 | Ntziachristos et al. | 600/312 |
| 2004/0021771 A1* | 2/2004 | Stearns et al. | 348/131 |
| 2007/0253908 A1* | 11/2007 | Rice et al. | 424/9.4 |

FOREIGN PATENT DOCUMENTS

| | | |
|---|---|---|
| JP | 7-250538 A | 10/1995 |
| JP | 10-165365 A | 6/1998 |
| JP | 2000-230807 A | 8/2000 |

OTHER PUBLICATIONS

Communication, dated Nov. 28, 2012, issued in corresponding EP Application No. 08021002.4, 7 pages.

* cited by examiner

*Primary Examiner* — Andrew W Johns  
(74) *Attorney, Agent, or Firm* — Sughrue Mion, PLLC

(57) ABSTRACT

There is provided an image processing system configured to correct an image of an object inside a physical body. The image processing system includes an object image obtaining section that obtains an object image formed by light from the object, a depth identifying section that identifies a depth from a surface of the physical body to the object, a distance information identifying section that identifies distance information indicating a distance from an image capturing section capturing the object image to the surface of the physical body, and an image correcting section that corrects the object image according to the distance information and the depth.

18 Claims, 11 Drawing Sheets

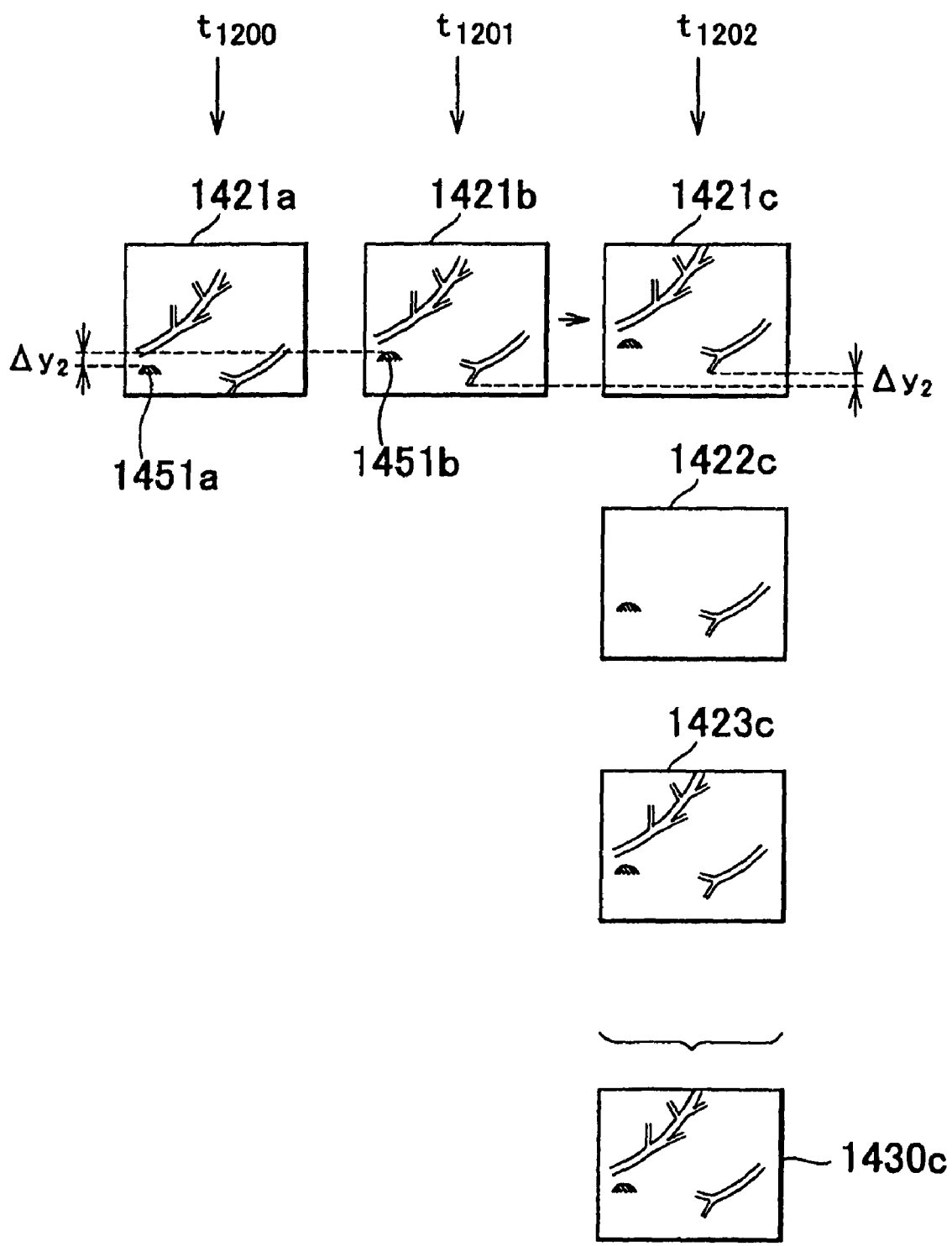
F I G. 12

IMAGE PROCESSING SYSTEM, IMAGE PROCESSING METHOD, AND COMPUTER READABLE MEDIUM

CROSS REFERENCE TO RELATED APPLICATION

The present application claims priority from a Japanese Patent Application No. 2007-314496 filed on Dec. 5, 2007, the contents of which are incorporated herein by reference.

BACKGROUND

1. Technical Field

The present invention relates to an image processing system, an image processing method and a computer readable medium. More particularly, the present invention relates to an image processing system and an image processing method for correcting an image of an object inside a physical body and to a computer readable medium storing therein a program for use with the image processing system.

2. Related Art

An endoscope disclosed in Japanese Patent Application Publication No. 10-165365 processes an image signal representing a predetermined range by using a point spread function of an objective optical system in order to clarify a blur of the image. Such a process is expected to be capable of clarifying a blur of the image caused by an insufficient focal depth of the objective optical system while increasing the amount of the light incident on the image capturing section.

A known measuring apparatus includes: a CCD camera that obtains binary information of a target physical body, to which artificial sunshine is irradiated in a darkroom, and displays the target physical body using dots on a CRT display; and a pair of laser emitters that are displayed on the target physical body as reference pointers as disclosed in, for example, Japanese Patent Application Publication No. 7-250538. The measuring apparatus calculates the area and peripheral length of the target physical body displayed on the CRT display with reference to the ratio between the distance between the reference pointers P1 and P2 displayed by using dots on the CRT display and the distance between the reference pointers on the actual target physical body, and then performs a comparison operation on the calculated area and peripheral length by using the ratio in order to know the position, shape and size of the target physical body. Furthermore, a known distance measuring apparatus includes: a CCD camera that is constituted by a fixed focus lens and a CCD of a photoelectric converter and that has a horizontal field angle of $\alpha$ and a vertical field angle of $\beta$; and laser light sources that are provided on the respective sides of the CCD camera with respect to an optical axis X-X with a predetermined interval LA/2 therebetween and emit a set of radial vertical parallel leaser light rays that have a radiation angle of $\theta$, as disclosed in, for example, Japanese Patent Application Publication No. 2000-230807.

For example, when an object such as a blood vessel inside a living organism is observed with the use of light from the object, only a blurry image is produced for the object. Specifically speaking, the light from the object is scattered while traveling through the living organism and the image of the object is vaguely outlined. Here, when making a diagnosis or performing an operation with the help of en endoscope, a medical doctor desires to accurately know the position of an object such as a blood vessel. Therefore, it is demanded to correct the blurry outline of the image of the object and thus provide the medical doctors with a clear image. The techniques disclosed in the above-mentioned three publications, however, cannot correct blurry images of objects inside physical bodies.

SUMMARY

Therefore, it is an object of an aspect of the innovations herein to provide an image processing system, an image processing method, and a computer readable medium which are capable of overcoming the above drawbacks accompanying the related art. The above and other objects can be achieved by combinations described in the independent claims. The dependent claims define further advantageous and exemplary combinations of the innovations herein.

To solve the above-mentioned problem, according to the first aspect related to the innovations herein, one exemplary image processing system may include an object image obtaining section that obtains an object image formed by light from an object inside a physical body, a depth identifying section that identifies a depth from a surface of the physical body to the object, a distance information identifying section that identifies distance information indicating a distance from an image capturing section capturing the object image to the surface of the physical body, and an object image correcting section that corrects the object image according to the distance information and the depth.

According to the second aspect related to the innovations herein, one exemplary image processing method may include obtaining an object image formed by light from an object inside a physical body, identifying a depth from a surface of the physical body to the object, identifying distance information indicating a distance from an image capturing section capturing the object image to the surface of the physical body, and correcting the object image according to the distance information and the depth.

According to the third aspect related to the innovations herein, one exemplary computer readable medium stores therein a program for use with an image processing system. When executed, the program causes the image processing system to function as an object image obtaining section that obtains an object image formed by light from an object inside a physical body, a depth identifying section that identifies a depth from a surface of the physical body to the object, a distance information identifying section that identifies distance information indicating a distance from an image capturing section capturing the object image to the surface of the physical body, and an image correcting section that corrects the object image according to the distance information and the depth.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

BRIEF DESCRIPTION OF THE DRAWINGS

FIG. 12 illustrates another exemplary method to generate a motion-compensated surface image.

DESCRIPTION OF EXEMPLARY EMBODIMENTS

Some aspects of the invention will now be described based on the embodiments, which do not intend to limit the scope of the present invention, but exemplify the invention. All of the features and the combinations thereof described in the embodiment are not necessarily essential to the invention.

Figure 1:
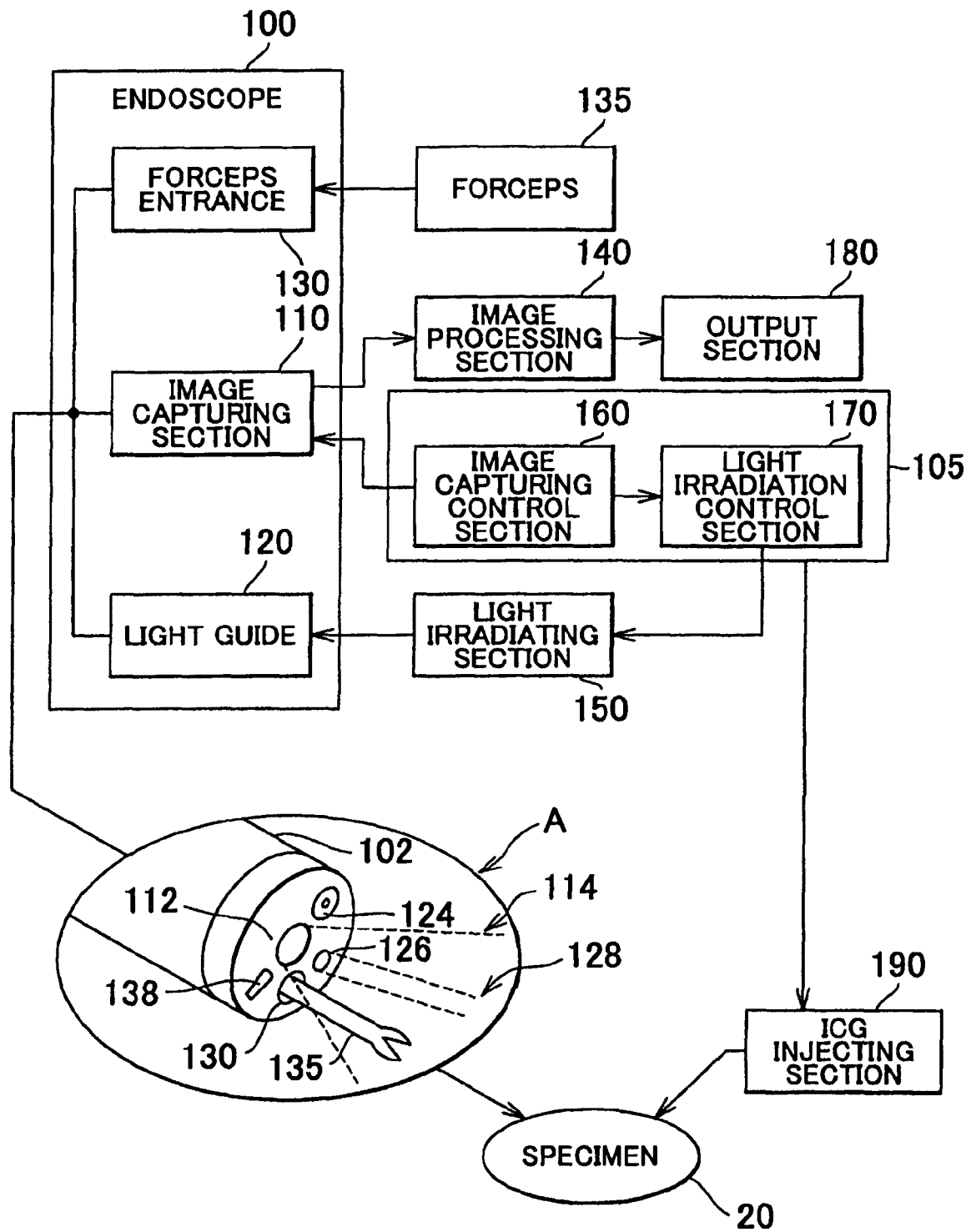
FIG. 1 illustrates an example of an image processing system 10 relating to an embodiment of the present invention, together with a specimen 20.

FIG. 1 illustrates an example of an image processing system 10 relating to an embodiment of the present invention, together with a specimen 20. The image processing system 10 is configured to correct an image of an object inside a physical body, according to the depth of the object. The image processing system 10 includes an endoscope 100, an image processing section 140, an output section 180, a control section 105, a light irradiating section 150, and an ICG injecting section 190. In FIG. 1, the reference character A indicates an enlargement view of an end portion 102 of the endoscope 100. The control section 105 includes an image capturing control section 160 and a light irradiation control section 170.

The ICG injecting section 190 injects indocyanine green (ICG) into the specimen 20, where indocyanine green serves as an luminescence substance and the specimen 20 is shown as an example of the physical body in the present invention. In the present embodiment, ICG is introduced as an example of the luminescence substance. Nonetheless, other fluorescent substances than ICG may be used as the luminescence substance. ICG is excited, for example, by an infra-red ray having a wavelength of 750 nm, to emit fluorescence with a broad spectrum having as its middle a wavelength of 810 nm.

When the specimen 20 is a living organism, the ICG injecting section 190 intravenously injects ICG into the blood vessels of the living organism. The image processing system 10 captures images of the blood vessels of the living organism with the use of luminescence light emitted from the ICG. Here, the luminescence light is shown as an example of the light from the physical body and includes fluorescence and phosphorescence. The luminescence light includes luminescence light produced by chemiluminescence, triboluminescence, or thermoluminescence in addition to photoluminescence caused by light such as excitation light. Here, a blood vessel may be shown as an example of the object in the present invention.

The ICG injecting section 190 injects ICG into the specimen 20, under the control of, for example, the control section 105, in such a manner that the ICG concentration within the living organism remains substantially constant. The specimen 20 may be a living organism, for example. In the specimen 20, there is an object such as a blood vessel. The image processing system 10 relating to the present embodiment detects the depth of an object from the surface of the specimen 20, where the object is underneath the surface of the specimen 20 (including the internal surface of an organ or the like). In addition, the image processing system 10 corrects the blurry image of the object according to the detected depth.

The endoscope 100 includes an image capturing section 110, a light guide 120, and a forceps entrance 130. The end portion 102 of the endoscope 100 has an objective lens 112, which forms a portion of the image capturing section 110. The end portion 102 also has a light exit 124 and a light exit 126, which form a portion of the light guide 120. The end portion 102 of the endoscope 100 further has a nozzle 138.

A forceps 135 is inserted into the forceps entrance 130, so that the forceps entrance 130 guides the forceps 135 through the end portion 102. The forceps 135 may have an end with any of various shapes. In addition to forcipes, a variety of treatment tools for treating living organisms may be inserted into the forceps entrance 130. The nozzle 138 sends out water or air.

The light irradiating section 150 generates light to be irradiated through the end portion 102 of the endoscope 100. The light generated by the light irradiating section 150 contains an infra-red ray and irradiation light, where the infra-red ray is shown as an example of excitation light that excites the luminescence substance in the specimen 20 to emit the luminescence light and the irradiation light is light irradiated to the specimen 20. The irradiation light includes R-component light, G-component light and B-component light, for example.

The image capturing section 110 captures images by using the luminescence light emitted from the luminescence substance and reflection light which is a portion of the irradiation light reflected by the object. The image capturing section 110 may include a two-dimensional image capturing device such as a CCD and an optical system, where the optical system contains the objective lens 112. When the luminescence substance emits infrared light, the image capturing section 110 can capture infrared light images. When the object is irradiated with light containing all of R, G and B components, for example, white light, the image capturing section 110 can capture visible light images.

The light from the object can be exemplified by luminescence light such as fluorescence or phosphorescence emitted by the luminescence substance in the object, or one of reflection light which is a reflected portion of the light irradiated to the object and transmission light which is a transmitted portion of the light irradiated to the object. In other words, the image capturing section 110 captures images of the object by using the light emitted from the luminescence substance in the object, the light reflected by the object, or the light transmitted by the object. Here, the image capturing section 110 can separately receive, in a time- or space-sharing manner, component light in the R wavelength range, component light in the G wavelength range, component light in the B wavelength range, and light in the luminescence light wavelength range.

The image capturing section 110 can capture images of the object by using any one of various methods, in addition to the method using the light from the object. For example, the image capturing section 110 may capture images of the object with the use of electromagnetic radiation such as X-rays or γ rays, or radiation containing corpuscular rays such as alpha rays. Alternatively, the image capturing section 110 may capture images of the object by using electromagnetic waves, radio waves or sound waves having a variety of wavelengths.

The light guide 120 can be formed by an optical fiber, for example. The light guide 120 is designed to guide the light generated by the light irradiating section 150 to the end portion 102 of the endoscope 100. The light guide 120 may include the light exits 124 and 126 formed in the end portion 102. The light generated by the light irradiating section 150 is irradiated to the specimen 20 through the light exits 124 and 126.

The light from the light exit 124 is irradiated so as to cover the image capturing range of the image capturing section 110. For example, the light from the light exit 124 is at least irradiated to a range, as defined by a line 114, from which the image capturing section 110 can receive light. On the other hand, the light from the light exit 126 is irradiated to the surface of a physical body in a direction substantially parallel to the image capturing direction of the image capturing section 110. For example, the light from the light exit 126 may be spot light, as indicated by a line 128, irradiated within the image capturing range of the image capturing section 110. The spot light mainly includes light substantially parallel to the image capturing direction of the image capturing section 110. With the use of the light from the light exit 124 and the light from the light exit 126, the image capturing section 110 can at least capture images of the surface of the physical body.

The image processing section 140 processes image data obtained from the image capturing section 110. The output section 180 outputs the image data processed by the image processing section 140. The image capturing control section 160 controls the image capturing operation by the image capturing section 110. The light irradiation control section 170 controls the light irradiating section 150, under the control of the image capturing control section 160. For example, when the image capturing section 110 captures images by using an infrared ray and the irradiation light in a time-sharing manner, the light irradiation control section 170 controls the light irradiating section 150 such that the irradiating timings of the infrared ray and irradiation light are synchronized with the image capturing timings by the image capturing section 110.

The image processing section 140 detects the depth of the object from the surface and the distance to the surface of the physical body from the image capturing section 110, with reference to the images captured by the image capturing section 110. According to the detected depth and distance, the image processing section 140 corrects the images of the object captured by the image capturing section 110.

Figure 2:
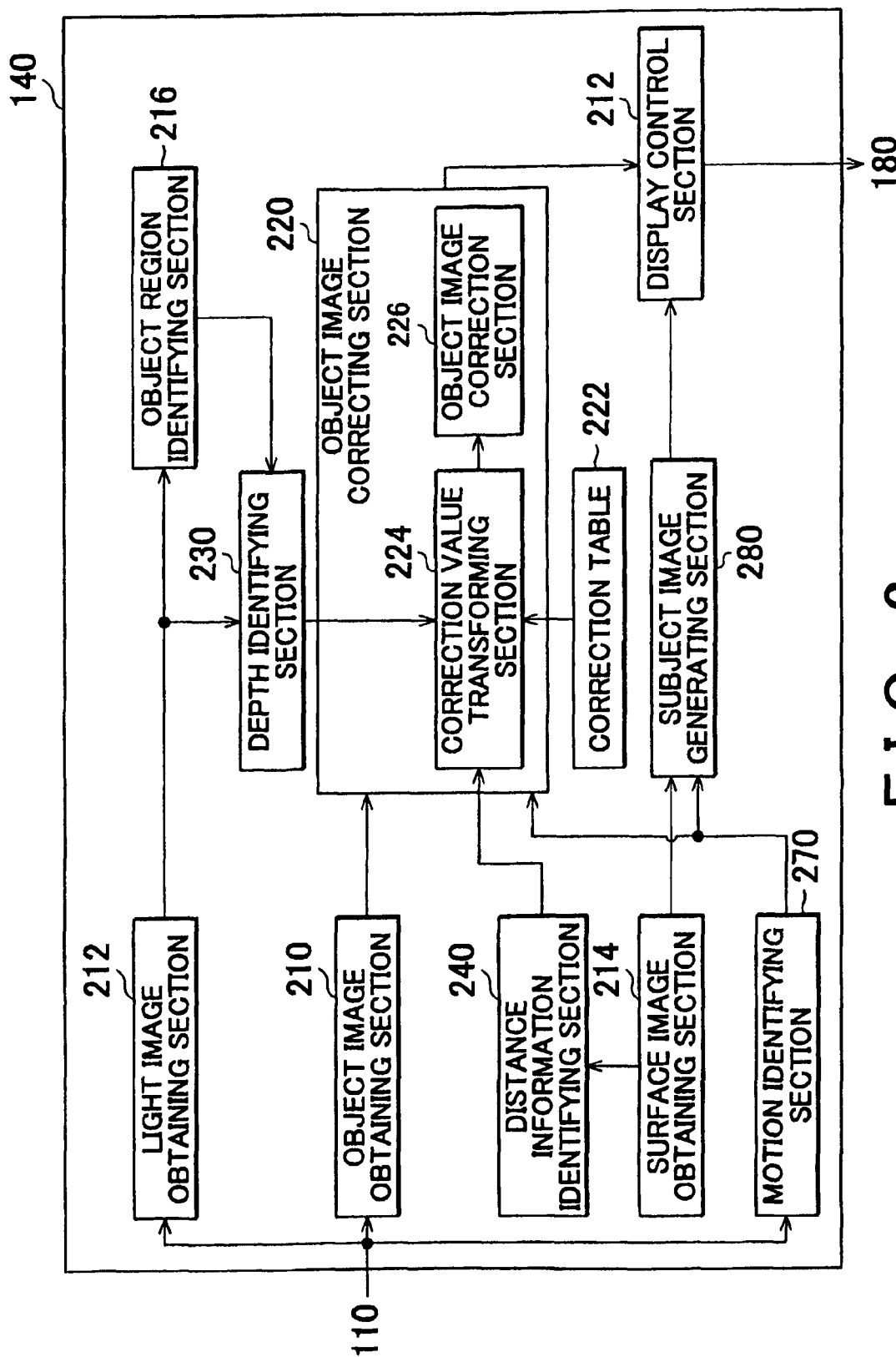
FIG. 2 illustrates an exemplary block configuration of an image processing section 140.

FIG. 2 illustrates an exemplary block configuration of the image processing section 140. The image processing section 140 includes an object image obtaining section 210, a light image obtaining section 212, a surface image obtaining section 214, an object region identifying section 216, an object image correcting section 220, a correction table 222, a distance information identifying section 240, a motion identifying section 270, a subject image generating section 280, a display control section 260, and a depth identifying section 230. The object image correcting section 220 includes a correction value transforming section 224 and an object image correction section 226.

The light image obtaining section 212 obtains a light image, which is an image formed by the light from the object such as a blood vessel inside the specimen 20. Specifically speaking, the light image obtaining section 212 obtains a light image, which is an image formed by the light from the object inside a physical body. To be more specific, the light image obtaining section 212 obtains, as a light image, the image captured by the image capturing section 110 by using the light from the object.

When the light from the object is the luminescence light emitted by the luminescence substance, the light image obtained by the light image obtaining section 212 includes an image of an object present between the surface of the physical body and a depth that can be reached by excitation light used to excite the luminescence substance. For example, the excitation light for the luminescence substance irradiated from the end portion 102 of the endoscope 100 has a wavelength of 750 nm. Therefore, this excitation light reaches a relatively large depth in the specimen 20 (for example, a depth of approximately several centimeters). In this case, the light image obtained by the light image obtaining section 212 includes an image of a blood vessel present at a relatively large depth in the specimen 20. Note that a blood vessel image may be an example of the light image in the present invention.

The excitation light excites a luminescence substance present within the depth that can be reached by the excitation light. Therefore, the light image obtained by the light image obtaining section 212 includes an image of a blood vessel present within the depth that can be reached by the excitation light. Here, the deeper a blood vessel is positioned, the more significantly the fluorescence from the blood vessel is scattered by the specimen 20. Hence, the deeper a blood vessel is positioned, the more blurry the image of the blood vessel is.

When the light from the object is the reflection light from the object, the light image obtained by the light image obtaining section 212 includes an object present within a depth that is reached by the irradiation light to the object and at which the irradiation light is reflected. Here, the depth that can be reached by the irradiation light to the physical body is dependent on the wavelength of the irradiation light. Specifically speaking, red light can reach a larger depth in a physical body than blue light, green light can reach an intermediate depth, and infrared light can reach a larger depth in a physical body than red light. Hence, the light image includes an image of an object present between the surface of a physical body and a reachable depth, which is dependent on the wavelength range of light irradiated to the physical body.

As described above, the light image obtaining section 212 obtains a plurality of light images each of which is captured by using light, from an object such as a blood vessel, in one of a plurality of different wavelength ranges. These wavelength ranges can be defined as needed and can be exemplified by a red range whose middle wavelength corresponds to the R component of visible light, a green range whose middle wavelength corresponds to the G component of visible light, and a blue range whose middle wavelength corresponds to the B component of visible light. Alternatively, these wavelength ranges may be obtained by dividing the wavelength range of the fluorescence from the ICG into a plurality of wavelength ranges and can be exemplified by a long wavelength range, an intermediate wavelength range, and a short wavelength range included in the wavelength range of the fluorescence from the ICG.

The depth identifying section 230 identifies the depth of an object such as a blood vessel, with reference to what is shown by a plurality of light images. For example, the depth identifying section 230 detects the depth of an object such as a blood vessel by making use of optical characteristics that light of a different wavelength can reach a different depth in the specimen 20, or by making use of different optical characteristics that light of a different wavelength exhibits a different absorptance in the specimen 20. Specifically speaking, the depth identifying section 230 judges that a blood vessel that can be observed in a blue-range light image is present within a depth at which light having a wavelength in the blue range is reflected. Similarly, the depth identifying section 230 judges that a blood vessel that can be observed in a green-range light image is present within a depth at which light having a wavelength in the green range is reflected. Furthermore, the depth identifying section 230 judges that a blood vessel that can be observed in a red-range light image is present within a depth at which light having a wavelength in the red range is reflected.

Referring to the fluorescence emitted from the ICG in the blood vessel, light in the long wavelength range is absorbed less than light in the short wavelength range. Therefore, the depth identifying section 230 estimates the depth of the blood vessel with reference to the ratio in brightness between the blood vessel images included in the light images respectively formed by the light in the long, intermediate and short wavelength ranges. For example, when a blood vessel image included in a light image formed by the light in the short wavelength range is dark in relation to the brightness of a blood vessel image included in a light image formed by the light in the long wavelength range, the depth identifying section 230 determines that the blood vessel is present at a deep position. Conversely, when a blood vessel image included in a light image formed by the light in the short wavelength range is bright in relation to the brightness of a blood vessel image included in a light image formed by the light in the long wavelength range, the depth identifying section 230 estimates that the optical path that would absorb the light in the short wavelength range is not long and that the blood vessel is thus present at a shallow position.

As described above, the depth identifying section 230 can detect the depth of an object such as a blood vessel by utilizing the optical characteristic that how deep in a physical body light can reach (the depth at which the light is reflected) is different depending on the wavelength of the light. In this case, the light image obtaining section 212 may obtain, as the light image, an image formed by the reflection light reflected by the object. The light image obtaining section 212 may obtain a plurality of light images, each of which is formed by light in one of a plurality of different wavelength ranges in the wavelength range of light reflected by the object when white light is irradiated to the object. Alternatively, the light image obtaining section 212 may obtain a plurality of light images, each of which is formed by light reflected by the object when light in one of a plurality of different wavelength ranges is irradiated to the object.

When the depth identifying section 230 detects the depth of an object such as a blood vessel by using the optical characteristic that fluorescence emitted at a deep portion of a physical body is absorbed at a different ratio depending on the wavelength as discussed above, the light image obtaining section 212 obtains a plurality of light images, each of which is formed by light in one of a plurality of different wavelength ranges included in the wavelength range of the light emitted from the luminescence substance in the object. The light irradiated to the object is emitted by the light irradiating section 150 and irradiated through the light exit 124.

As explained above, since light images have information regarding how deep light can reach, the depth identifying section 230 can calculate the depth of an object by comparing or performing an operation on the brightness (luminance) levels of the objects in the light images. For example, the object region identifying section 216 identifies image regions showing an object in a plurality of light images constituting each light image set. The depth identifying section 230 then identifies the depth from the surface to the object based on the luminance levels of the image regions identified by the object region identifying section 216.

For example, the depth identifying section 230 identifies the depth by referring to the ratio of the luminance of the image region in the short wavelength range light image to the luminance of the image region in the long wavelength range light image. Alternatively, the depth identifying section 230 may identify the depth based on the maximum or average luminance among the image regions.

As a further alternative example, the depth identifying section 230 may identify the depth by referring to the luminance change ratios at the edges of the object image regions. This luminance change ratio can be expressed as, for example, a derivative of the luminance that varies according to the position (distance) in the image space. This derivative is an example of numerical representation indicating how blurry the object is in the image region. As the derivative increases, the blur decreases and the estimated position of the object becomes shallower.

The luminance change ratio can be expressed as, for example, a half bandwidth of the distribution of the luminance that varies according to the position (distance) in the image space. As the half bandwidth increases, the blur increases. As the half bandwidth decreases, the estimated position of the object becomes shallower. In the above-described manner, the depth identifying section 230 can identify the depth from the surface of the physical body to the object.

The distance information identifying section 240 identifies the distance from the image capturing section 110, which captures light images, to the surface of a physical body. In the present invention, distance information may be a distance in the real space itself or an indicator of the distance in the real space. In the following description, a reference to "a distance" indicates the distance from the image capturing section 110 to the surface of the physical body, unless otherwise stated.

For example, the surface image obtaining section 214 obtains an image including a surface image, which is an image of the surface of a physical body formed by light irradiated to the surface of the physical-body in a direction substantially parallel to the image capturing direction of the image capturing section 110. The distance information identifying section 240 then identifies the distance based on the size of the surface image included in the image obtained by the surface image obtaining section 214. Here, the substantially parallel light may be the spot light emitted from the light irradiating section 150 and irradiated through the light exit 126.

The object image obtaining section 210 obtains an object image captured by using the light from the object. The image capturing section 110 may capture an image of the object through the surface. The object image obtaining section 210 obtains the image of the object which is captured through the surface. For example, the object image obtaining section 210 obtains an object image captured by the image capturing section 110 by using the luminescence light from the object.

The object image correcting section 220 corrects the object image according to the distance identified by the distance information identifying section 240 and the depth identified by the depth identifying section 230. Specifically speaking, the object image correcting section 220 corrects the object image according to the distance identified by the distance information identifying section 240 and the depth identified by the depth identifying section 230. More specifically, the object image correcting section 220 corrects the spread of the object image according to the distance identified by the distance information identifying section 240 and the depth identified by the depth identifying section 230. To be further specific, the object image correcting section 220 corrects the spread of the object image, which is caused because the light from the object is scattered between the object and the surface, according to the distance identified by the distance information identifying section 240 and the depth identified by the depth identifying section 230.

The corrected image obtained as a result of the correction by the object image correcting section 220 is supplied to the output section 180 and displayed by the output section 180. The correction table 222 stores a correction value in association with a depth from a surface to an object, where the correction value is used to correct spread of an object image. The object image correcting section 220 corrects the spread of the object image, with reference to the distance identified by the distance information identifying section 240, the depth identified by the depth identifying section 230, and a corresponding correction value stored on the correction table 222.

The surface image obtaining section 214 obtains an image of a physical body surface that is captured by the image capturing section 110, as one example. In other words, the surface image obtaining section 214 obtains the same image as visually observed. For example, the surface image obtaining section 214 obtains, as the surface image, an image captured by the image capturing section 110 by using a portion of the irradiation light which is reflected by the surface of the physical body. For example, the surface image obtaining section 214 obtains, as the surface image, the image captured by the image capturing section 110 by using a portion of the irradiation light which is reflected by the surface of the physical body, where the irradiation light is white light.

The image capturing section 110 may capture an object image and a surface image at different timings. For example, the image capturing section 110 may successively capture a surface image with visible light by irradiating white light and capture an object image by irradiating excitation light in place of white light at a predetermined timing. In this case, the motion identifying section 270 identifies a motion of the object made between the excitation light irradiation timing and the white light irradiation timing. The subject image generating section 280 generates a surface image which is supposed to be obtained at the excitation light irradiation timing, based on the surface image obtained by the irradiation of the white light and the motion identified by the motion identifying section 270. How the control section 105, the image capturing section 110, the light irradiating section 150, the motion identifying section 270 and the subject image generating section 280 function and operate to capture an object image and a surface image in a time-sharing manner is described in more detail with reference to FIG. 6 and subsequent drawings.

The display control section 260 controls how a surface image and a corrected image are displayed through the output section 180. For example, the display control section 260 controls how to display the object image corrected by the object image correcting section 220, according to the depth identified by the depth identifying section 230. Specifically speaking, the display control section 260 changes the brightness or color of the object image corrected by the object image correcting section 220 according to the depth and causes the output section 180 to display the resultant image. Alternatively, the display control section 260 may cause the output section 180 to display a surface image and a corrected image next to each other. Furthermore, the display control section 260 may cause the output section 180 to display a numerical value indicating object depth information.

The following describes the operations of the constituents of the object image correcting section 220. The object image correcting section 220 includes the correction value transforming section 224 and the object image correction section 226. The correction table 222 stores a correction value for the real space in association with a depth of an object from a surface. In other words, the correction table 222 stores a correction value for the real scale. In this case, the correction value transforming section 224 transforms a correction value for the real space stored on the correction table 222 into a correction value appropriate for an object image, according to the distance identified by the distance information identifying section 240.

The object image correction section 226 corrects the spread of the object image by using the correction value appropriate for the object image obtained by the correction value transforming section 224. In this manner, the object image correcting section 220 can appropriately correct the blurry object image according to the position of the surface.

The depth identifying section 230 may identify the depth of each of a plurality of objects from the surface. The depth identifying section 230 may calculate the depth of each of a plurality of objects from the surface. The object image correcting section 220 may correct spread of an image of each of a plurality of objects in an object image, according to the depth of each of the plurality of objects.

Figure 3:
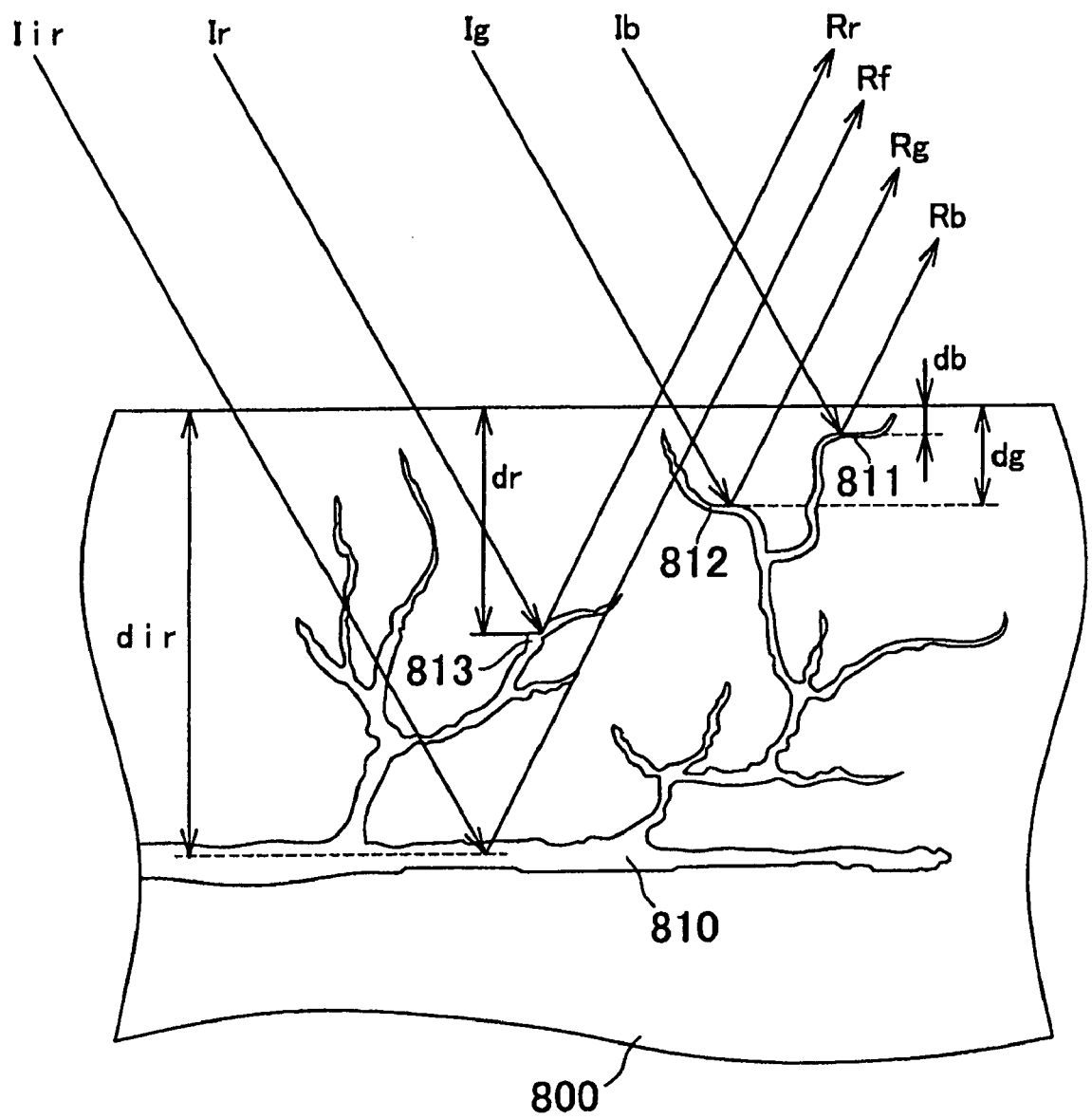
FIG. 3 schematically illustrates how light is, for example, reflected inside the specimen 20.

FIG. 3 schematically illustrates how light is, for example, reflected inside the specimen 20. Inside the specimen 20, there is a blood vessel 810, which is an exemplary object. Here, ICG, which is an exemplary luminescence substance, is injected into a blood vessel. Therefore, ICG is in the blood vessel 810. The specimen 20 is irradiated with infrared light Iir, which is designed to excite the ICG, and red light Ir, green light Ig, and blue light Ib which are irradiated to the blood vessel 810, which is an exemplary object.

The infrared light Iir can reach a relatively deep position (having a depth dir) in the specimen 20, and excites the ICG in the blood vessel 810 from the surface to the depth dir. Therefore, an image of the blood vessel 810 within the depth dir is captured with the use of fluorescence Rf emitted from the ICG, to produce an object image. Note that the image of the blood vessel 810, which is obtained as an object image, is blurry.

The red light Ir reaches a depth dr and is reflected in the vicinity of the depth dr. Therefore, red reflection light Rr of the red light Ir contains image information regarding a portion of the blood vessel 810 in the vicinity of the depth dr. The image of the blood vessel 810 formed by the red reflection light Rr is obtained as a light image formed by the red wavelength range light. This light image includes an image showing the portion of the blood vessel 810 in the vicinity of the depth dr.

The green light Ig reaches a depth dg and is reflected in the vicinity of the depth dg. Therefore, green reflection light Rg of the green light Ig contains image information regarding a portion of the blood vessel 810 in the vicinity of the depth dg. The image of the blood vessel 810 formed by the green reflection light Rg is obtained as a light image formed by the green wavelength range light. This light image includes an image showing the portion of the blood vessel 810 in the vicinity of the depth dg.

The blue light Ib reaches a depth db and is reflected in the vicinity of the depth db. Therefore, blue reflection light Rb of the blue light Ib contains image information regarding a portion of the blood vessel 810 in the vicinity of the depth db. The image of the blood vessel 810 formed by the blue reflection light Rb is obtained as a light image formed by the blue wavelength range light. This light image includes an image showing the portion of the blood vessel 810 in the vicinity of the depth db.

As mentioned above, the depth identifying section 230 can identify the depth of the blood vessel 810 based on the light images formed by the red reflection light Rr, the green reflection light Rg, and the blue reflection light Rb. The object image correcting section 220 can correct the object image formed by the fluorescence Rf according to the depth identified by the depth identifying section 230.

Figure 4:
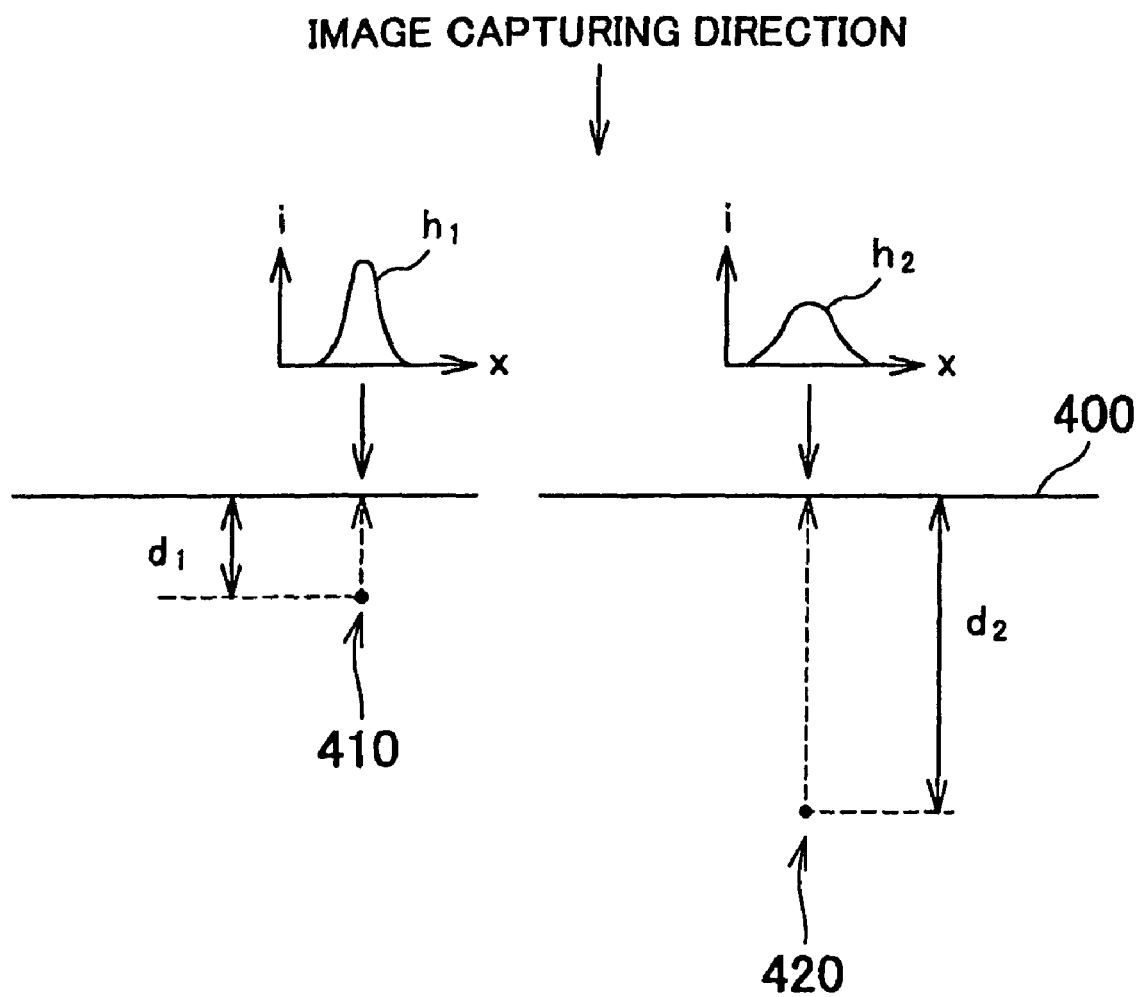
FIG. 4 schematically illustrates how light from the inside of the specimen 20 becomes blurry.

FIG. 4 schematically illustrates how the light from the inside of the specimen 20 becomes blurry. It is assumed that a point light source is present at a position 410 in the specimen 20 away from the surface 400 of the specimen 20 by a depth d1. The light from the point light source to the image capturing section 110 is scattered by the specimen 20 while traveling from the position 410 to the surface 400, so as to have a luminance distribution designated by h1 at the surface 400. Here, x denotes a real-space x coordinate within a plane vertical to the image capturing direction.

Here, it is also assumed that a point light source is present at a position 420 in the specimen 20 away from the surface 400 of the specimen 20 by a depth d2. The light from the point light source to the image capturing section 110 is scattered by the specimen 20 while traveling from the position 420 to the surface 400, so as to have a luminance distribution designated by h2 at the surface 400. In FIG. 4, the spread is shown one-dimensionally, but the luminance distribution at the surface is two-dimensional.

As seen from the distributions in FIG. 4, the deeper the point light source is positioned, the broader the light from the point light source is at the surface. For this reason, an object image formed by light from an object at the position 420 is more blurry than an object image formed by light from an object at the position 410. Here, since the spread is dependent the depth from the surface to the point light source, the degree of the spread is defined in the real space scale. Therefore, a point spread function in the real space is associated with a depth of an object. Consequently, when the depth identifying section 230 identifies a depth in terms of the image capturing direction of the image capturing section 110 and the distance information identifying section 240 identifies a distance to a surface, the object image correcting section 220 can correct spread of an object image, with reference to a point spread function associated with the identified depth and distance.

For example, the correction table 222 stores an inverse filter of a point spread function whose parameter is a depth. The correction value transforming section 224 transforms the stored inverse filter into an inverse filter that is applied to an image, according to a distance identified by the distance information identifying section 240. The object image correction section 226 corrects each object image identified by the object region identifying section 216 by using an inverse filter obtained by the correction value transforming section 224.

Alternatively, the correction table 222 may store an inverse filter of a point spread function whose parameters are a depth and a distance. The object image correction section 226 may correct each object image identified by the object region identifying section 216 by using an inverse filter associated with the distance identified by the distance information identifying section 240 and the depth identified by the depth identifying section 230.

Figure 5:
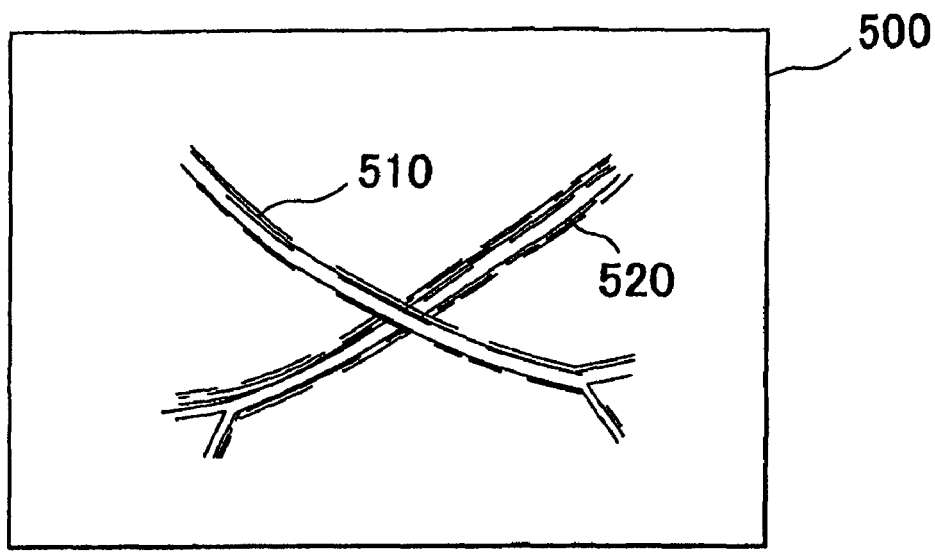
FIG. 5 illustrates exemplary blood vessel images 560 and 570 obtained as a result of correction by an object image correcting section 220.
Figure 5:
Figure 5:
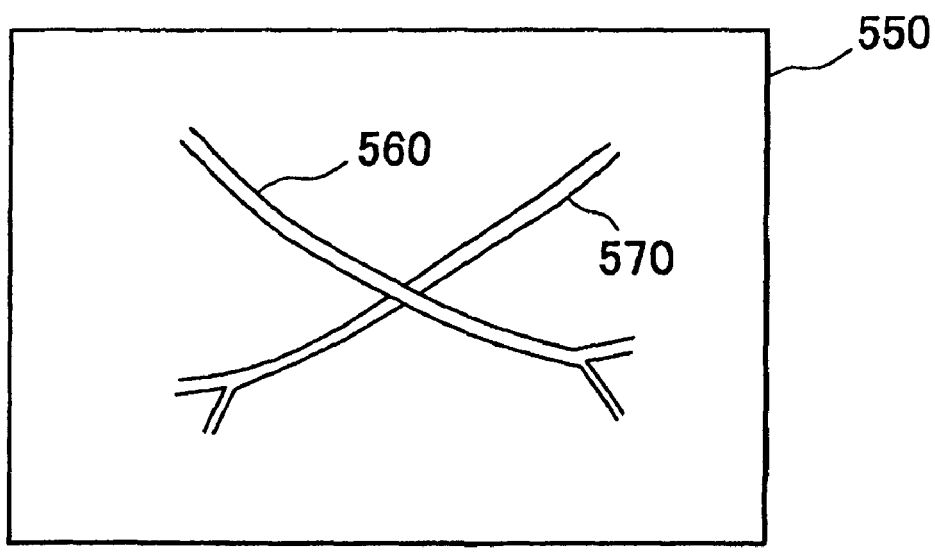

FIG. 5 illustrates exemplary blood vessel images 560 and 570 obtained as a result of the correction by the object image correcting section 220. An image 500 captured by the image capturing section 110 includes blurry blood vessel images 510 and 520. Note that the blood vessel image 510 shows a blood vessel at a shallower position than the blood vessel image 520 and that the blood vessel image 510 is less blurry than the blood vessel image 520.

The image obtained by the surface image obtaining section 214 includes a surface image formed by the spot light irradiated in a direction substantially parallel to the image capturing direction of the image capturing section 110. The surface image captured by the image capturing section 110 with the use of a portion of the spot light which is reflected by the surface shows a portion on the surface to which the spot light is irradiated. The distance information identifying section 240 identifies the distance between the image capturing section 110 and the surface by referring to the size of the surface image formed by the spot light. For example, the distance information identifying section 240 may identify the distance between the image capturing section 110 and the surface by referring to at least one of the diameter and the area of the surface image formed by the spot light.

The spot light emitted through the light exit 126 may have a substantially circular projected image on a plane perpendicular to its travel direction. When the shape of the spotlight is known, the distance information identifying section 240 may identify the distance between the image capturing section 110 and the surface further with reference to the shape of the surface image formed by the spot light. For example, when the spot light has a circular shape, the distance information identifying section 240 may identify the distance between the image capturing section 110 and the surface with reference to the minor axis of the surface image. Furthermore, when the spot light has a circular shape, the distance information identifying section 240 may identify the distance between the image capturing section 110 and the surface further with reference to the degree with which the surface image is similar to an ellipse. With such a configuration, the distance information identifying section 240 can identify the distance based on the size and shape of the surface image even when the spot light is not vertically incident on the surface.

The depth identifying section 230 can also calculate a depth from a surface to a blood vessel in the above-described manner. The object region identifying section 216 extracts the regions of the blood vessel images 510 and 520 from the image 500, as blood vessel regions. The object image correcting section 220 corrects the regions of the blood vessel images 510 and 520 identified by the object region identifying section 216 with the use of inverse filters associated with the distance from the surface to the image capturing section 110 and the depths of the blood vessels identified by the depth identifying section 230, as described above.

To sum up, the object image correcting section 220 increases the correction to be performed on spread of an object image as a depth increases. The object image correcting section 220 also increases the correction to be performed on spread of an object image as a distance indicated by distance information decreases. For example, since the blood vessel image 510 shows a blood vessel at a shallower position than the blood vessel image 520, the object image correcting section 220 corrects the blur of the blood vessel image 520 more significantly than the blur of the blood vessel image 510.

The object image correcting section 220 corrects the blurry blood vessel image 510 and outputs a blood vessel image 560 to the display control section 260. In addition, the object image correcting section 220 corrects the blurry blood vessel image 520 and outputs a blood vessel image 570 to the display control section 260. The display control section 260 causes the output section 180 to display the depths from the surface, for example, by using different gradation levels or colors. Use of the image processing system 10 relating to the present embodiment may make it possible for medical doctors to have a clear view of internal blood vessels, which are not visible from the surface, for example, when the medical doctors perform operations and the like with their eyes on the display provided by the output section 180. In addition, the medical doctors may advantageously be capable of performing operations and the like while being provided with information regarding the depths of the internal blood vessels.

In the present embodiment, the light irradiation control section 170 may control the light irradiation intensity according to the distance identified by the distance information identifying section 240. For example, the light irradiation control section 170 may decrease the intensity of the light irradiated from the light irradiating section 150 as the distance identified by the distance information identifying section 240 decreases. The light irradiation control section 170 may stop the light irradiation from the light irradiating section 150, when the distance identified by the distance information identifying section 240 exceeds a predetermined value. Here, the distance information identifying section 240 may identify the distance to the surface, for example, based on irradiation of ultrasound wave or laser to the surface.

Figure 6:
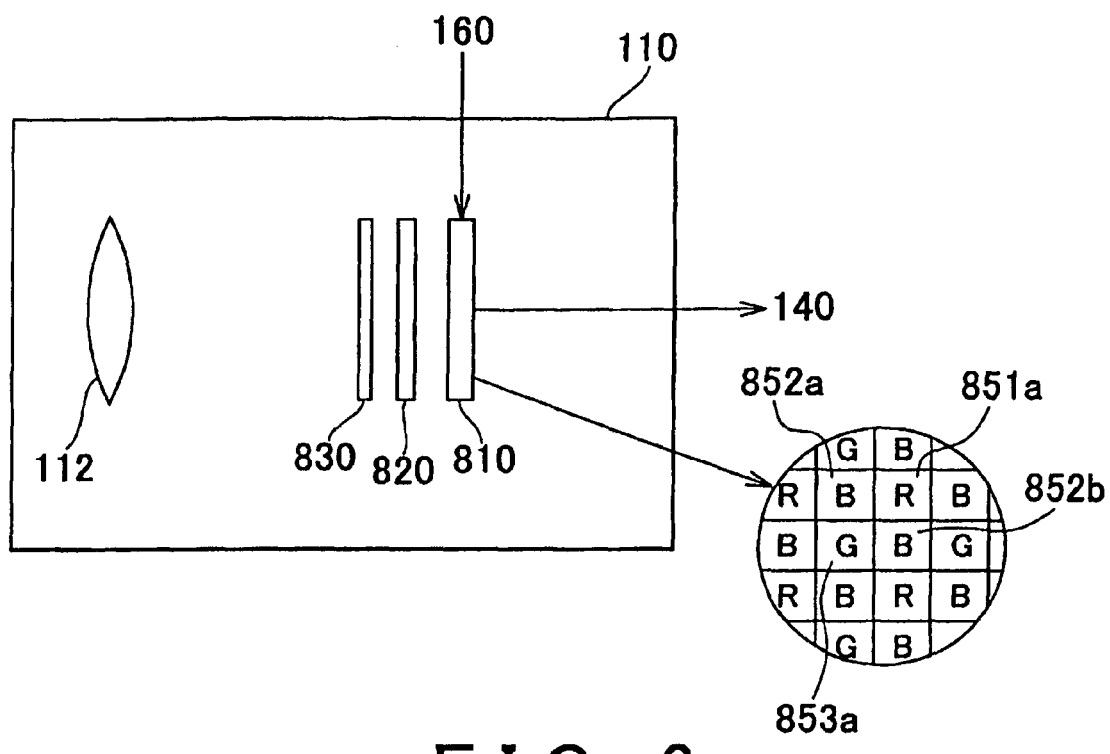
FIG. 6 illustrates an exemplary configuration of an image capturing section 110.

FIG. 6 illustrates an exemplary configuration of the image capturing section 110. The image capturing section 110 includes an objective lens 112, an image capturing device 810, a spectral filter section 820, and a reception-side excitation light cut filter section 830. The image capturing device 810 includes a plurality of first light receiving elements 851 having a first light receiving element 851a, a plurality of second light receiving elements 852 having second light receiving elements 852a and 852b, and a plurality of third light receiving elements 853 having a third light receiving element 853a.

The following describes the functions and operations of the constituents of the image capturing section 110. To make the following description simple, the plurality of first light receiving elements 851 may be collectively referred to as the first light receiving elements 851, the plurality of second light receiving elements 852 may be collectively referred to as the second light receiving elements 852, and the plurality of third light receiving elements 853 may be collectively referred to as the third light receiving elements 853. Also, the plurality of first light receiving elements 851, the plurality of second light receiving elements 852, and the plurality of third light receiving elements 853 may be collectively and simply referred to as the light receiving elements.

The first, second and third light receiving elements 851, 852 and 853 receive light from a subject through the objective lens 112. Specifically speaking, the first light receiving elements 851 receive light in a specified wavelength range and light in a first wavelength range different from the specified wavelength range. The specified wavelength range may be exemplified by the infrared range, such as the wavelength range of the luminescence light. The second light receiving elements 852 receive light in a second wavelength range different from the specified wavelength range. The third light receiving elements 853 receive light in a third wavelength range different from the first, second and specified wavelength ranges.

The first, second and third wavelength ranges are different from each other, and do not overlap each other. The first, second and third light receiving elements 851, 852 and 853 are arranged two-dimensionally in a predetermined pattern.

The spectral filter section 820 includes a plurality of filter elements each of which transmits light in one of the first, second and third wavelength ranges. The filter elements are arranged two-dimensionally in accordance with the first, second and third light receiving elements 851, 852 and 853. Each light receiving element receives light transmitted by corresponding one filter element. In this manner, the first, second and third light receiving elements 851, 852 and 853 receive light in different wavelength ranges.

The reception-side excitation light cut filter section 830 is provided at least between the subject and the second and third light receiving elements 852 and 853, and cuts off light in the excitation light wavelength range. In this manner, the second and third light receiving elements 852 and 853 receive reflection light from the subject through the reception-side excitation light cut filter section 830. With such a configuration, the second and third light receiving elements 852 and 853 substantially does not receive a portion of the excitation light reflected by the subject.

The reception-side excitation light cut filter section 830 may cut off light in the excitation light wavelength range and light in the specified wavelength range. In this case, the second and third light receiving elements 852 and 853 receive substantially no luminescence light from the subject, for example.

The reception-side excitation light cut filter section 830 may be provided between the subject and the first light receiving elements 851. In this case, the reception-side excitation light cut filter section 830 provided between the subject and the first light receiving elements 851 is configured to transmit the light in the specified wavelength range.

The reception-side excitation light cut filter section 830 may include filter elements arranged two-dimensionally in accordance with the first, second and third light receiving elements 851, 852 and 853, similarly to the spectral filter section 820. In this case, the filter elements supplying light to the first light receiving elements 851 at least transmit the light in the first and specified wavelength ranges. The filter elements supplying light to the first light receiving elements 851 may cut off the light in the excitation light wavelength range. The filter elements supplying light to the second light receiving elements 852 cut off the light in the excitation light and specified wavelength ranges and at least transmit the light in the second wavelength range. The filter elements supplying light to the third light receiving elements 853 cut off the light in the excitation light and specified wavelength ranges and at least transmit the light in the third wavelength range.

The image processing section 140 determines the pixel value of one pixel based at least on the amount of light received by the first light receiving element 851a, the second light receiving element 852a, the second light receiving element 852b and the third light receiving element 853a. In other words, a two-dimensional arrangement of the first light receiving element 851a, the second light receiving element 852a, the second light receiving element 852b and the third light receiving element 853a forms a single pixel element. By arranging such arrangements two-dimensionally, a plurality of pixel elements are formed. How to arrange the light receiving elements is not limited to the configuration shown in FIG. 6 and may be modified in a variety of manners.

Figure 7:
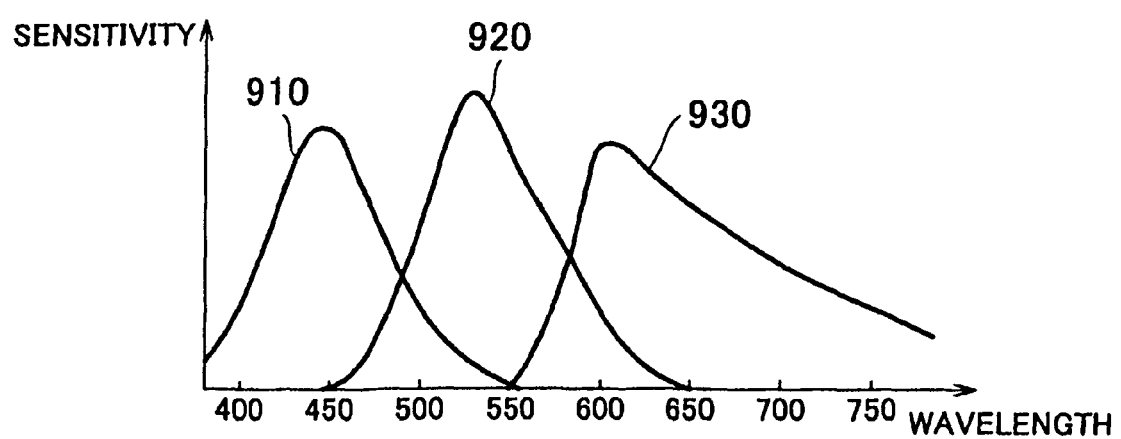
FIG. 7 illustrates exemplary spectral sensitivity characteristics of first, second and third light receiving elements 851, 852 and 853.

FIG. 7 illustrates exemplary spectral sensitivity characteristics of the first, second and third light receiving elements 851, 852 and 853. Lines 930, 910, and 920 respectively show spectral sensitivity distributions of the first, second and third light receiving elements 851, 852 and 853. For example, the first light receiving elements 851 are sensitive to light having a wavelength in the vicinity of 650 nm, where the other light receiving elements are substantially insensitive to 650 nm. The second light receiving elements 852 are sensitive to light having a wavelength in the vicinity of 450 nm, where the other light receiving elements are substantially insensitive to 450 nm. The third light receiving elements 853 are sensitive to light having a wavelength in the vicinity of 550 nm, where the other light receiving elements are substantially insensitive to 550 nm.

Also, the first light receiving elements 851 can receive light in the infrared range (for example, 810 nm), which is an example of the specified wavelength range. The above-described spectral sensitivity characteristics are dependent on the transmission characteristics of the reception-side excitation light cut filter section 830 and spectral filter section 820 and the spectral sensitivities of the light receiving elements.

Having the above-described configurations, the first, second and third light receiving elements 851, 852 and 853 respectively receive R-component light, B-component light and G-component light. The first light receiving elements 851 can also receive light in the infrared range, which is an example of the specified wavelength range. The first, second and third light receiving elements 851, 852 and 853 may be image capturing elements such as CCDs or CMOSs, for example. The first, second and third light receiving elements 851, 852, and 853 respectively have spectral sensitivity characteristics shown by the lines 930, 910 and 920, which are determined by the spectral transmittance of the reception-side excitation light cut filter section 830, the spectral transmittances of the filter elements included in the spectral filter section 820, and the spectral sensitivities of the image capturing elements.

Figure 8:
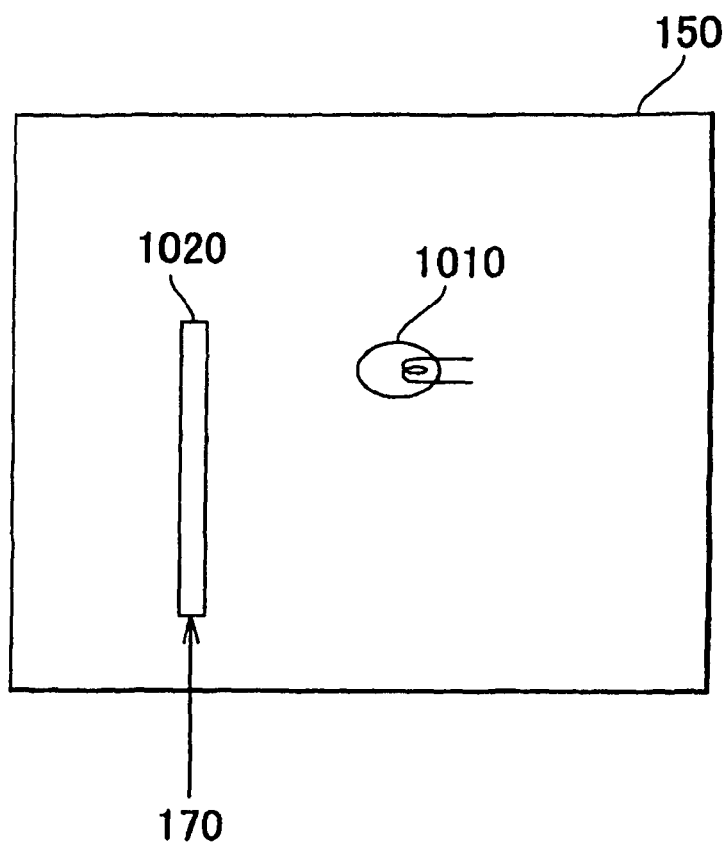
FIG. 8 illustrates an exemplary configuration of a light irradiating section 150.

FIG. 8 illustrates an exemplary configuration of the light irradiating section 150. The light irradiating section 150 includes a light emitting section 1010 and a source-side filter section 1020. The light emitting section 1010 emits light whose wavelength range covers the excitation light, first, second and third wavelength ranges. In the present embodiment, the light emitting section 1010 may be a xenon lamp, as an example.

Figure 9:
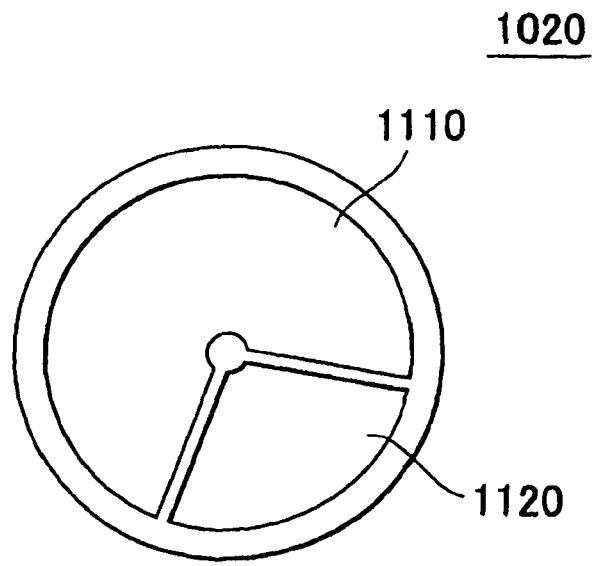
FIG. 9 illustrates an exemplary configuration of a source-side filter section 1020.

FIG. 9 illustrates an exemplary configuration of the source-side filter section 1020. FIG. 9 illustrates the configuration of the portion of the source-side filter section 1020 which faces the light emitting section 1010. The source-side filter section 1020 includes an irradiation light cut filter section 1120 and an excitation light cut filter section 1110. The light irradiation control section 170 rotates the source-side filter section 1020 with respect to the central axis of the source-side filter section 1020 within a plane substantially perpendicular to the direction in which the light emitted by the light emitting section 1010 travels.

The excitation light cut filter section 1110 transmits the light in the first wavelength range, the light in the second wavelength range, and the light in the third wavelength range, and substantially cuts off the light in the excitation light wavelength range. The irradiation light cut filter section 1120 transmits the light in the excitation light wavelength range, the light in the second wavelength range and the light in the third wavelength range. It is preferable that the irradiation light cut filter section 1120 substantially cuts off the light in the first wavelength range. The light from the light emitting section 1010 is guided to a position off the central axis of the source-side filter section 1020.

Therefore, when the light from the light emitting section 1010 is guided to the excitation light cut filter section 1110, the light in the excitation light wavelength range, out of the light from the light emitting section 1010, is substantially cut off by the excitation light cut filter section 1110, and the light in the first wavelength range, the light in the second wavelength range and the light in the third wavelength range are transmitted by the excitation light cut filter section 1110. Therefore, at this timing, the light in the first wavelength range, the light in the second wavelength range and the light in the third wavelength range are substantially irradiated to the subject.

On the other hand, when the light from the light emitting section 1010 is guided to the irradiation light cut filter section 1120, the light in the excitation light wavelength range, the light in the second wavelength range and the light in the third wavelength range, out of the light from the light emitting section 1010, are transmitted by the irradiation light cut filter section 1120. Therefore, at this timing, the excitation light, the light in the second wavelength range and the light in the third wavelength range are substantially irradiated to the subject.

The image capturing section 110 receives reflection light reflected from the specimen 20, when the light in the first wavelength range, the light in the second wavelength range, and the light in the third wavelength range are irradiated to the specimen 20, under the control of the image capturing control section 160. Here, the light in the first wavelength range, the light in the second wavelength range, and the light in the third wavelength range are visible light. Based on the amount of the light received by the image capturing section 110, the surface image obtaining section 214 generates a subject image by using the visible light, where the subject image is an example of the surface image. When the irradiated light is substantially white light, the surface image may be referred to as a white light image.

The image capturing section 110 receives the luminescence light emitted by the ICG in the subject, a portion of the light in the second wavelength range which is reflected by the specimen 20, and a portion of the light in the third wavelength range which is reflected by the specimen 20, when the excitation light, the light in the second wavelength range, and the light in the third wavelength range are irradiated to the specimen 20, under the control of the image capturing control section 160. The object image obtaining section 210 obtains a signal corresponding to the amount of the light received by the first light receiving elements 851 from the first light receiving elements 851, and generates a subject image of luminescence light based on the amount of the luminescence light received by the first light receiving elements 851. The surface image obtaining section 214 generates a subject image of visible light based on the received amount of the light in the second wavelength range corresponding to a signal from the second light receiving elements 852, the received amount of the light in the third wavelength range corresponding to a signal from the third light receiving elements 853, and the amount of the light in the first wavelength range received by the first light receiving elements 851 at a different timing.

Figure 10:
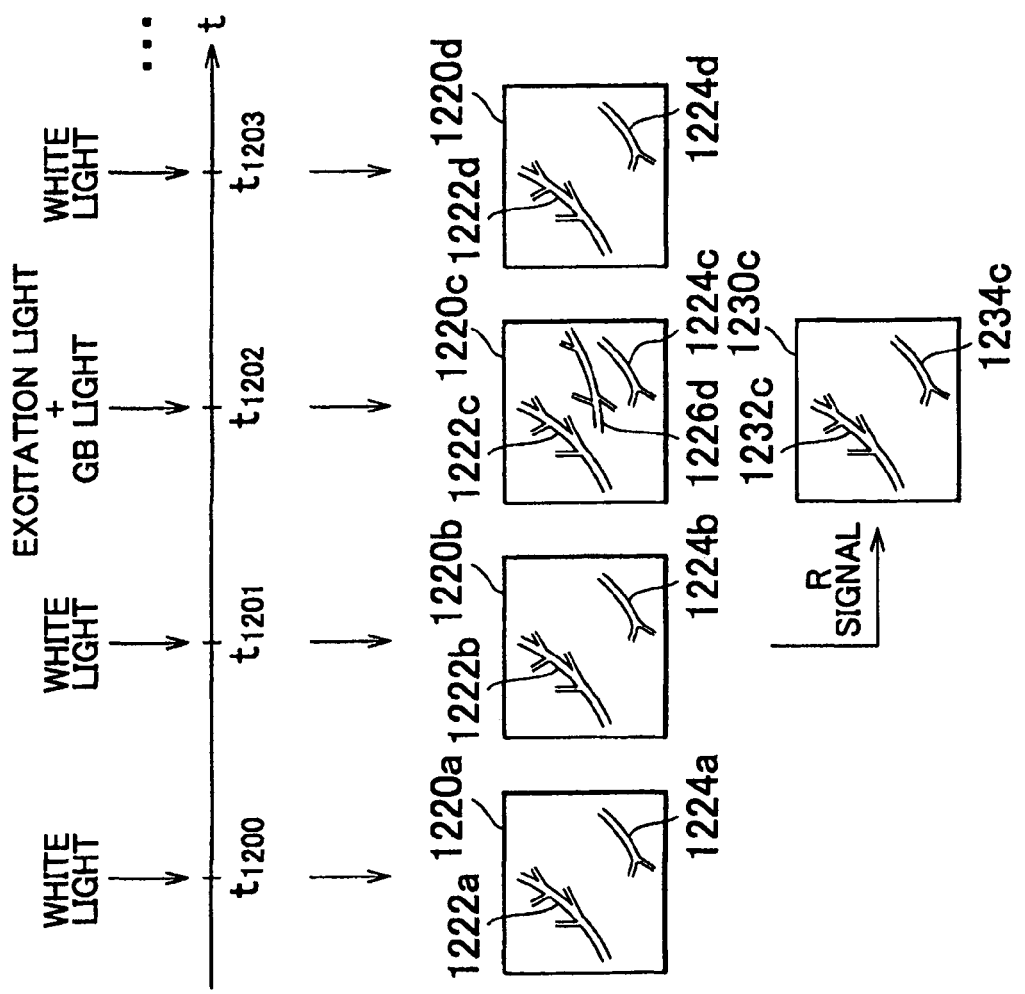
FIG. 10 illustrates the image capturing timings of the image capturing section 110 and exemplary images generated by the image processing section 140.

FIG. 10 illustrates the image capturing timings of the image capturing section 110 and exemplary images generated by the image processing section 140. The image capturing control section 160 causes the image capturing section 110 to capture images by using light from an object at times t1200, t1201, t1202, t1203, . . . . The light irradiation control section 170 causes the light emitted by the light emitting section 1010 to be irradiated to the subject through the excitation light cut filter section 1110 at a first timing exemplified by the times t1200, t1201, and t1203, under the timing control of the image capturing control section 160. As stated here, under the control of the light irradiation control section 170, the light irradiating section 150 irradiates the subject with light whose wavelength range covers the first, second and third wavelength ranges at the first timing.

At the first timing, the image capturing control section 160 controls the first light receiving elements 851 to receive the light in the first wavelength range, controls the second light receiving elements 852 to receive the light in the second wavelength range, and controls the third light receiving elements 853 to receive the light in the third wavelength range, where the received light is included in the reflection light reflected by the subject when the subject is irradiated with the light whose wavelength range covers the first, second and third wavelength ranges. In other words, at the first timing, the image capturing control section 160 controls the first light receiving elements 851 to receive the light in the first wavelength range from the subject, controls the second light receiving elements 852 to receive the light in the second wavelength range from the subject, and controls the third light receiving elements 853 to receive the light in the third wavelength range from the subject.

On the other hand, at a second timing exemplified by the time t1202, the light irradiation control section 170 controls the light emitted from the light emitting section 1010 to be irradiated to the subject through the irradiation light cut filter section 1120, under the timing control of the image capturing control section 160. In other words, at the second timing, the light irradiating section 150 irradiates the subject with the light whose wavelength range covers the excitation light wavelength range, the second wavelength range and the third wavelength range, under the control of the light irradiation control section 170.

At the second timing, the image capturing control section 160 controls the first light receiving elements 851 to receive the light in the specified wavelength range emitted by the subject. That is to say, the image capturing control section 160 controls the first light receiving elements 851 to receive the light in the specified wavelength range from the subject at the second timing.

As described above, at the second timing, the control section 105 controls the light in the first wavelength range not to be irradiated to the subject and controls the excitation light, the light in the second wavelength range and the light in the third wavelength range to be irradiated to the subject, so that the first light receiving elements 851 receive the light in the specified wavelength range emitted by the subject, the second light receiving elements 852 receive the light in the second wavelength range out of the reflection light from the subject and the third light receiving elements 853 receive the light in the third wavelength range out of the reflection light from the subject. The excitation light wavelength range is different from any of the first, second and third wavelength ranges, and does not overlap any of the first, second and third wavelength ranges.

As described above, the control section 105 controls the spectrum of the light received by the first light receiving elements 851, the spectrum of the light received by the second light receiving elements 852 and the spectrum of the light received by the third light receiving elements 853. The image processing section 140 generates an image by using light having various wavelength ranges based on the amount of light received by the light receiving elements at each timing.

Specifically speaking, the surface image obtaining section 214 generates subject images 1220a, 1220b, and 1220d based on the amount of light received by the light receiving elements at timings exemplified by the times t1200, t1201 and t1203. The subject images 1220a, 1220b, and 1220d can be substantially treated as visible light images obtained when white light is irradiated. The subject image 1220a includes a blood vessel image 1222a and a blood vessel image 1224a, the subject image 1220b includes a blood vessel image 1222b and a blood vessel image 1224b, and the subject image 1220d includes a blood vessel image 1222d and a blood vessel image 1224d.

In addition to the blood vessel images, the subject images 1220a, 1220b, and 1220d include surface images showing a surface of a physical body. As explained above, the surface image obtaining section 214 generates a surface image of a subject at a first timing, by using the light in the first wavelength range received by the first light receiving elements 851 at the first timing, the light in the second wavelength range received by the second light receiving elements 852 at the first timing, and the light in the third wavelength range received by the third light receiving elements 853 at the first timing.

The object image obtaining section 210 generates a subject image 1220c including blood vessel images 1222c, 1224c, and 1226c, based on the amount of light received by the light receiving elements at a timing exemplified by the time t1202. The subject image 1220c can be treated as a subject image formed by luminescence light from a subject. The subject image 1220c is subjected to the above-described blur correcting operation by the object image correcting section 220.

The subject image generating section 280 generates a subject image 1230c including blood vessel images 1232c and 1234c, based on the amount of the light received by the first light receiving elements 851 at a timing exemplified by the time t1201, the amount of light received by the second light receiving elements 852 at a timing exemplified by the time t1202 and the amount of the light received by the third light receiving elements 853 at the timing exemplified by the time t1202. The subject image 1230c can be treated as a subject image of visible light that is supposed to be obtained at the timing exemplified by the time t1202.

As described above, the image processing section 140 generates a subject image of visible light for the second timing, by using the light in the first wavelength range received by the first light receiving elements 851 at the first timing and the light in the second wavelength range received by the second light receiving elements 852 at the second timing. Hence, the image processing section 140 can generate an image of visible light even at a timing where a luminescence light image is captured. The output section 180 successively displays the subject images 1220a, 1220b, 1230c, 1220d, . . . , thereby providing a video image with no frames dropped.

When the specimen 20 is a living organism having red bloods, for example, a human body, a visible light image is usually characterized in that the R component has a smaller spatial frequency component than the G and B components. For this reason, image degradation is usually less significant when the R-component frame images are dropped than when the G- and B-component frame images are dropped. The above-described configuration can thus reduce the awkwardness in the resulting video image, when compared with the case where the G- and B-component frame images are dropped. As a result, the image processing system 10 may be capable of providing a visible light video image with substantially no frame images dropped.

As discussed above, the image processing system 10 can capture the subject image 1220c by using the luminescence light in the infrared wavelength range generated from the specimen 20 by the excitation light in the infrared region. Having a longer wavelength than visible light, the excitation light is more difficult to be absorbed by a physical matter than visible light. Therefore, the excitation light can reach a larger depth (for example, approximately 1 cm) in a physical matter than visible light and causes the specimen 20 to emit luminescence light. The luminescence light has a further longer wavelength than the excitation light and thus can easily reach the surface of the physical matter. As a consequence, the image processing system 10 can provide the subject image 1220c including a blood vessel image 1226d showing a blood vessel in a very deep region, which is not included in the subject images 1220a, 1220b and 1220d obtained by visible light.

The output section 180 may generate a combined image by combining the subject image 1220c and one of the subject images 1220b and 1220d captured at timings in the vicinity of the timing at which the subject image 1220c is captured and output the combined image to outside. For example, the output section 180 may display the combined image. Alternatively, the output section 180 may record the subject image 1220c in association with one of the subject images 1220b and 1220d.

At a timing where a visible light image is captured, the control section 105 cuts off light in the excitation light wavelength range and light in the luminescence light wavelength range in the light from the light emitting section 1010, and irradiates the subject with the resultant light. Therefore, the image processing system 10 can provide a visible light image showing a surface of a physical matter, which shows no blood vessels inside the physical matter and thus is suitable for the physical matter surface observation.

Figure 11:
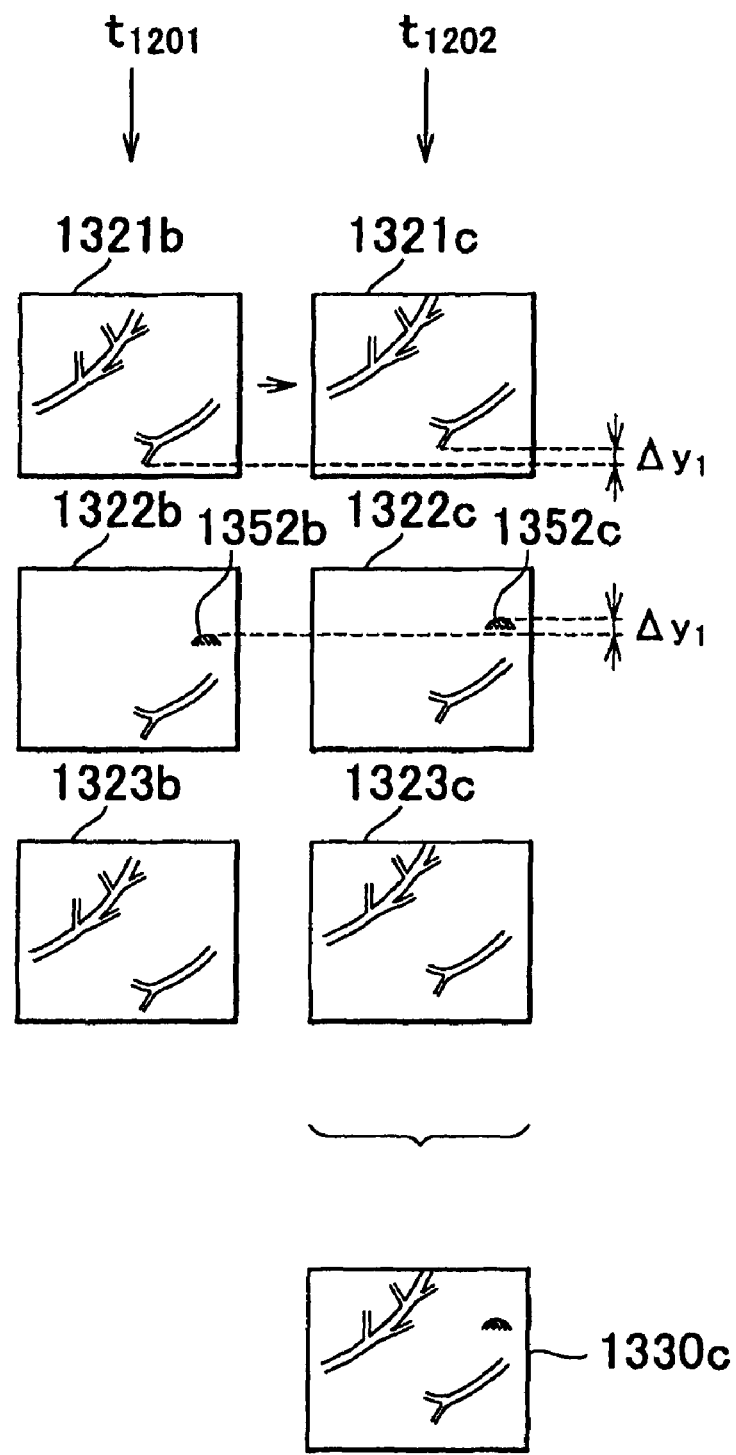
FIG. 11 illustrates how to generate a motion-compensated surface image.

FIG. 11 illustrates how to generate a motion-compensated surface image. FIG. 10 is used to describe an exemplary operation to generate the subject image 1230c by multiplexing the R signal corresponding to the amount of the light received by the first light receiving elements 851 at the time t1201 with the B and G signals corresponding to the amount of the light received by the second light receiving elements 852 at the time t1202 and the amount of the light received by the third light receiving elements 853 at the time t1202, under an assumption that there are no factors to trigger a significant change in images over time, such as motion of the end portion 102 of the endoscope 100 and motion of the specimen 20 for the sake of intelligibility. Referring to the operation, in fact, motion of the end portion 102 of the endoscope 100, motion of the specimen 20 and the like may cause a disagreement between the R signal and the other color signals in the visible light image.

With reference to FIGS. 11 and 12, the following describes the operations and functions of the image processing section 140 to correct the influence on the visible light image by various factors including the above-mentioned motions, especially with a main focus on the operations of the motion identifying section 270 and the subject image generating section 280.

The motion identifying section 270 uses images formed by the B signal at a plurality of timings to identify a motion of an object among those images. Here, the motion of the object is a motion that causes a change in the images over time, and is exemplified by the motion of the specimen 20, the motion of the end portion 102 of the endoscope 100, and the change over time in the zoom value of the image capturing section 110. The motion of the end portion 102 of the endoscope 100 includes a change over time in the position of the end portion 102 which causes a change over time in the image capturing position of the image capturing section 110, and a change over time in the facing direction of the end portion 102 which causes a change over time in the image capturing direction of the image capturing section 110.

The motion identifying section 270 identifies the motion of the object based on the B-signal images at the times t1201 and t1202. For example, the motion identifying section 270 may identify the motion of the object by attempting to match objects extracted from a plurality of images to each other.

The subject image generating section 280 corrects an R signal obtained at the time t1201 according to the identified motion, to generate an R signal that is supposed to be obtained at the time t1202. The subject image generating section 280 then multiplexes together the R signal generated by the compensation process, the B signal obtained at the time t1202, and the G signal obtained at the time t1202, to generate a surface image for the time t1202.

An image 1321b is formed by the R signal from the first light receiving elements 851 at the time t1201. Images 1322b and 1322c are respectively formed by the B signal from the second light receiving elements 852 at the times t1201 and t1202. Images 1323b and 1323c are respectively formed by the G signal from the third light receiving elements 853 at the times t1201 and t1202.

In the present example, the motion identifying section 270 identifies the motion by referring to what is shown in the images 1322b and 1322c. Specifically speaking, the motion identifying section 270 extracts objects showing the same subject from the images 1322b and 1322c. According to the example shown in FIG. 11, the motion identifying section 270 extracts objects 1352b and 1352c from the images 1322b and 1322c.

The motion identifying section 270 calculates the difference in position between the objects 1352b and 1352c. According to the example shown in FIG. 11, it is assumed that the difference in position is seen in a y direction on the images for the intelligibility. In such a case, the motion identifying section 270 calculates the positional difference Δy1 between the objects 1352b and 1352c.

The subject image generating section 280 shifts the image 1321b in the y direction by an amount determined in accordance with the calculated positional difference Δy1, thereby generating an image 1321c. The subject image generating section 280 combines the images 1321c, 1322c, and 1323c, to generate a surface image 1330c. Here, the combining process includes multiplexing the R signal representing the image 1321c, the B signal representing the image 1322c and the G signal representing the image 1323c with predetermined weights.

According to the above description, the motion is identified by using the images 1322 formed by the B signal. In a similar manner, however, the motion can be identified by using the images 1323 formed by the G signal. The motion identifying section 270 may identify a motion by using images in one of the wavelength ranges which is selected based on the contrast levels of the captured images. For example, the motion identifying section 270 may identify a motion by using the highest contrast images with the highest priority. The motion identifying section 270 may be capable of more accurately identifying a motion by using B-signal images when microstructure images can be used for motion identification, which may become possible because clear images are available for microstructures on a surface. Furthermore, the motion identifying section 270 may be capable of more accurately identifying a motion by using G-signal images when concave and convex structure images can be used for motion identification, which may become possible because clear images are available for concave and convex structures on a surface.

The subject image generating section 280 may compensate the motion in an R-signal image by a different amount in each image region. For example, when the image capturing direction of the image capturing section 110 is perpendicular to the surface of the subject and the end portion 102 of the endoscope 100 moves horizontally with respect to the surface of the subject, the amount of the motion of an object can be assumed to be the same in every image region. On the other hand, when the image capturing direction of the image capturing section 110 is not perpendicular to the surface of the subject, for example, the amount of the motion may be smaller in an image region showing a distant region from the end portion 102 than in an image region showing a close region to the end portion 102.

In order that the subject image generating section 280 calculates the degree of the motion compensation on an R-signal image for each image region, the positional relation between the surface of the subject and the image capturing section 110 may need to be known or estimated. Based on the positional relation and the position of each image region, the subject image generating section 280 can calculate the degree of the motion compensation for each image region. The subject image generating section 280 may obtain control values used for operating the endoscope 100, which may influence changes over time in images, such as control values used for controlling the position and facing direction of the end portion 102 and control values used to control the zoom value of the image capturing section 110 and calculate the degree of the motion compensation on an R-signal image with reference to the obtained control values.

Alternatively, the motion identifying section 270 may calculate a motion of an object in each image region. The subject image generating section 280 may calculate the degree of the motion compensation on each image region based on the identified motion of the object in each image region.

When identifying a motion in each image region, the motion identifying section 270 may identify the motion in each image region by using images formed by light in one of the wavelength ranges which is determined in association with each image region. For example, the motion identifying section 270 calculates the contrast of each image in units of image regions. The motion identifying section 270 may select, in association with each image region, images formed by light in a wavelength range for which the highest contrast is calculated in the highest priority compared with images formed by light in the other wavelength ranges, and identify a motion of an object by using the selected images.

As described above with reference to FIGS. 10 and 11, the motion identifying section 270 uses an image formed by the light in the second wavelength range received by the second light receiving elements 852 at a first timing and an image formed by the light in the second wavelength range received by the second light receiving elements 852 at a second timing in order to identify a motion of an object on the images between the first and second timings. The subject image generating section 280 generates a surface image of the second timing, by using the light in the first wavelength range received by the first light receiving elements 851 at the first timing, the light in the second wavelength range received by the second light receiving elements 852 at the second timing and the identified motion.

FIG. 12 illustrates another exemplary method to generate a motion-compensated surface image. According to the example shown in FIG. 12, the motion identifying section 270 identifies a motion of an object by using an R-signal image 1421a obtained at the time t1200 and an R-signal image 1421b obtained at the time t1201. Similarly to the method described with reference to FIG. 11, the motion identifying section 270 extracts objects showing the same subject from the images 1421a and 1421b. According to the example shown in FIG. 12, the motion identifying section 270 extracts objects 1451a and 1451b respectively from the images 1421a and 1421b.

The motion identifying section 270 then calculates the difference in position between the objects 1451a and 1451b. According to the example shown in FIG. 12, it is also assumed that the difference in position is seen in a y direction on the images for the intelligibility. In such a case, the motion identifying section 270 calculates the positional difference $\Delta y2$ between the objects 1451a and 1451b. In the same manner as described with reference to FIG. 11, the subject image generating section 280 generates an image 1421c by shifting the image 1421b in the y direction by an amount determined in accordance with the calculated positional difference $\Delta y2$. The subject image generating section 280 combines the image 1421c, an image 1422c formed by the B signal from the second light receiving elements 852 at the time t1202, and an image 1423c formed by the G signal from the third light receiving elements 853 at the time t1202, thereby generating a surface image 1430c.

According to the above description, the images 1421a and 1421b are used to identify the motion. The motion identifying section 270, however, may identify the motion by using the image 1421b and an R-signal image obtained at a time t1203. In other words, the motion identifying section 270 may identify a motion by using images obtained at a plurality of timings including timings preceding and following the time t1202 for which a motion-compensated R-signal image is generated. When it is permitted to display a visible light image with a delay to a certain degree, the motion identifying section 270 may be capable of identifying a motion more accurately by using an image captured at a later timing.

As described above with reference to FIG. 12, the motion identifying section 270 uses a plurality of images formed by the light in the first wavelength range received by the first light receiving elements 851 at a plurality of timings including not a second timing but a first timing, in order to identify a motion of an object on the images between the timings. The subject image generating section 280 generates a surface image for the second timing, with reference to the light in the first wavelength range received by the first light receiving elements 851 at the first timing, the light in the second wavelength range received by the second light receiving elements 852 at the second timing, and the identified motion.

According to the exemplary motion identifying operations described with reference to FIGS. 11 and 12, the motion identifying section 270 identifies a motion by using images captured at two timings. The motion identifying section 270, however, may identify a motion by using images captured at three or more timings. Furthermore, the motion identifying section 270 can select, for each image region, images of a particular wavelength range in order to identify a motion, from R-signal images in addition to B-signal and G-signal images.

The object image correcting section 220 can use the motion identified by the motion identifying section 270 in order to identify which blood vessel images 1222 and 1224 in different subject images 1220 correspond to the blood vessel images 1222c and 1224c included in the subject image 1220c, when performing the above-described blur correction on the subject image 1220c.

The second and third light receiving elements 852 and 853 are sensitive to light in the luminescence light wavelength range, and may receive luminescence light from a subject at a timing exemplified by the time t1202. In this case, the spectral filter section 820 and the reception-side excitation light cut filter section 830 may transmit the light in the luminescence light wavelength range.

In this case, the object image obtaining section 210 may generate an object image by performing pixel addition processing. Specifically speaking, the object image obtaining section 210 adds together image signals from a plurality of light receiving elements in the vicinity of each other, which are selected from the first, second and third light receiving elements 851, 852 and 853. Here, an image signal from a light receiving element may be a signal indicating a charge amount determined in accordance with the amount of light received by the light receiving element. This signal representing the charge amount may be an analog signal determined by the amount of light received by the light receiving element, or a digital signal obtained by A/D converting the analog signal. Any pixel addition processing can increase a signal component. Here, an increase in a random noise component caused by the pixel addition processing is smaller than the increase in the signal component caused by the pixel addition processing. Therefore, the above configuration can improve the S/N ratio when compared with a case where pixel addition processing is not applied.

In the same manner as described with reference to FIGS. 11 and 12, the motion identifying section 270 can identify a motion by using the R-signal, G-signal or B-signal images obtained at a plurality of timings excluding a timing exemplified by the time t1202. The subject image generating section 280 can generate a visible light subject image which is supposed to be obtained at the timing exemplified by the time t1202 by correcting, according to the identified motion, a visible light subject image obtained at a timing excluding the timing exemplified by the time t1202.

According to the above description of the exemplary configuration of the light irradiating section 150, a single light source and a rotation filter are used, where the light source can emit light whose wavelength range includes the visible light wavelength range and the excitation light wavelength range. As an alternative example, the light irradiating section 150 can emit visible light and light containing excitation light in a time-sharing manner, by controlling light emission of a plurality of light emitting elements each of which is designed to emit light in one of a plurality of different wavelength ranges. For example, a light emitting element designed to emit visible light can be exemplified by a semiconductor element such as an LED, and a light emitting element designed to emit excitation light can be exemplified by a semiconductor element such as semiconductor laser. Alternatively, a light emitting element can be formed by using a fluorescence substance that emits luminescence light such as fluorescence when excited.

The light irradiation control section 170 can make it possible to emit visible light and light containing excitation light in a time-sharing manner, by controlling the light emission intensity of each light emitting element at each timing. Here, "controlling the light emission intensity of each light emitting element at each timing" includes controlling a different combination of light emitting elements to emit light at each timing.

The light emitting elements may be provided at the end portion 102 of the endoscope 100. The light emitting elements may emit light when electrically or optically excited. When the light emitting elements emit light when optically excited, the light irradiating section 150 may include the light emitting elements and an exciting section that emits light for exciting the light emitting elements. The light emitting elements may emit light having a different spectrum according to the wavelength of the excitation light. In this case, the light irradiation control section 170 can control the spectrum of irradiation light by controlling the wavelength of the excitation light emitted by the exciting section at each timing. When the plurality of light emitting elements are excited by the same excitation light, each light emitting element may emit light with a different spectrum. Here, a portion of the excitation light which passes through the light emitting elements may be irradiated to a subject as irradiation light.

According to the above description of the exemplary configuration of the image capturing section 110, the spectral filter section 820 is provided at the light-reception side. As an alternative configuration, the image capturing section 110 may not include the spectral filter section 820. In this case, the light irradiating section 150 may provide light in the R wavelength range, light in the G wavelength range, light in the B wavelength range, and light in the excitation light wavelength range in a time-sharing manner. The surface image obtaining section 214 can generate a visible light subject image by multiplexing together signals from a plurality of light receiving elements at timings where visible light is irradiated. The object image obtaining section 210 can generate a luminescence light subject image by using a signal from a light receiving element at a timing where excitation light is irradiated.

To provide light in the R wavelength range, light in the G wavelength range, light in the B wavelength range, and light in the excitation light wavelength range in a time-sharing manner, the light irradiating section 150 may be configured by including one or more light sources that can emit light whose wavelength range includes the above-mentioned visible light and excitation light wavelength ranges and a rotation filter that includes a plurality of filter sections each mainly and selectively transmitting light in a corresponding one of the wavelength ranges. Alternatively, the light irradiating section 150 may be configured so as to control light emission of a plurality of light emitting elements each of which is designed to emit light in a different wavelength range, as described above.

Even when light in each wavelength range is irradiated in a time-sharing manner, the motion identifying section 270 can identify a motion by using image signals of one color component obtained at a plurality of timings, in the same manner as described with reference to FIGS. 11 and 12. The subject image generating section 280 may use, for example, an R-signal image obtained at a timing where the light in the R wavelength range is irradiated and the identified motion in order to generate an R-signal image which is supposed to be obtained at a different timing at which the light in the R wavelength range is not irradiated. In a similar manner, the subject image generating section 280 generates a G-signal image for a timing at which the light in the G wavelength range is not irradiated and a B-signal image for a timing at which the light in the B wavelength range is not irradiated. In this way, the subject image generating section 280 can generate a visible light surface image which is supposed to be obtained at each timing.

Figure 13:
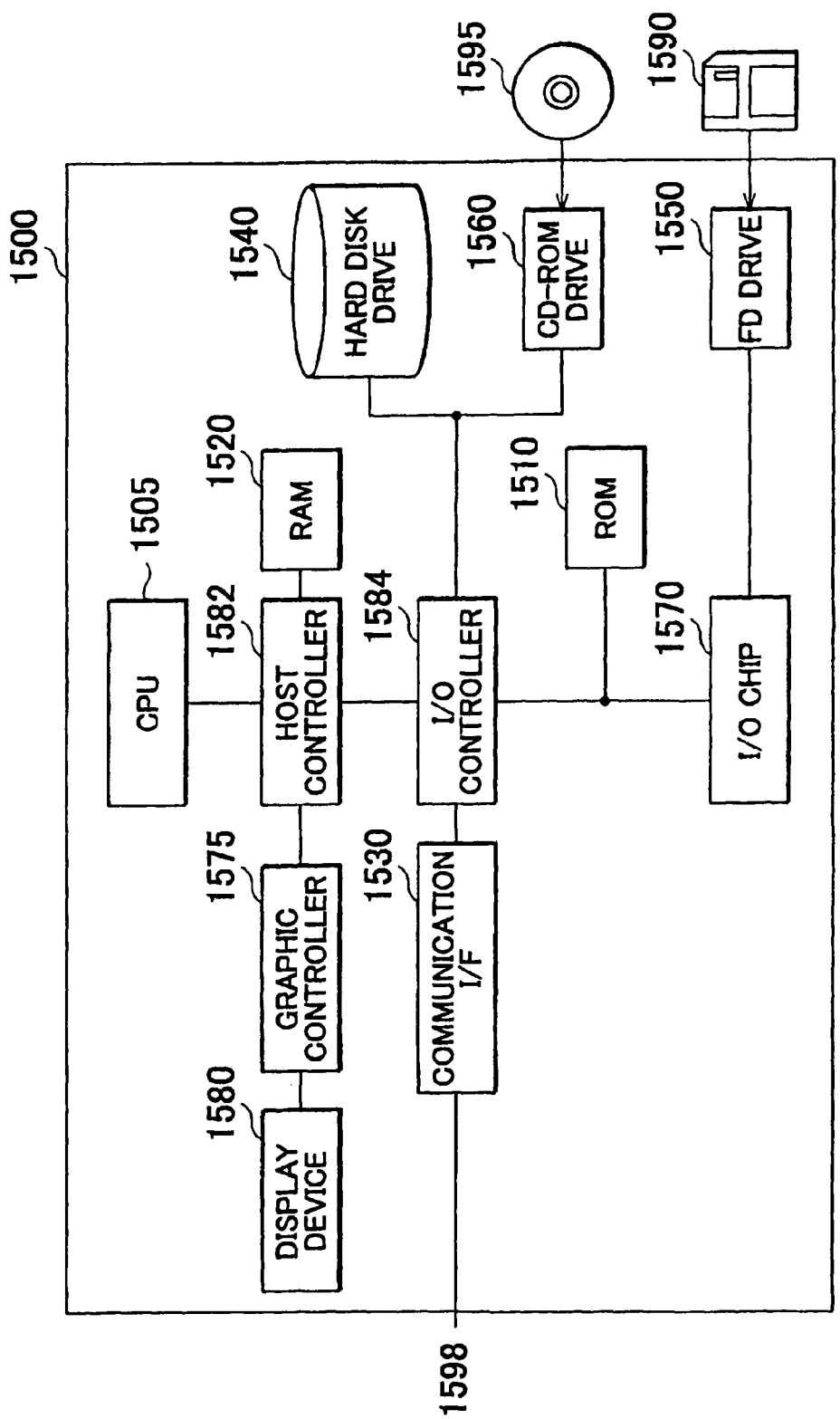
FIG. 13 illustrates an exemplary hardware configuration of the image processing system 10 relating to the embodiment of the present invention.

FIG. 13 illustrates an exemplary hardware configuration of the image processing system 10 relating to the embodiment of the present invention. The image processing system 10 relating to the present embodiment is constituted by a CPU peripheral section, an input/output (I/O) section and a legacy I/O section. The CPU peripheral section includes a CPU 1505, a RAM 1520, a graphic controller 1575 and a display device 1580 which are connected to each other by means of a host controller 1582. The I/O section includes a communication interface 1530, a hard disk drive 1540, and a CD-ROM drive 1560 which are connected to the host controller 1582 by means of an I/O controller 1584. The legacy I/O section includes a ROM 1510, a flexible disk drive 1550, and an I/O chip 1570 which are connected to the I/O controller 1584.

The host controller 1582 connects the RAM 1520 with the CPU 1505 and graphic controller 1575 which access the RAM 1520 at a high transfer rate. The CPU 1505 operates in accordance with programs stored on the ROM 1510 and RAM 1520, to control the constituents. The graphic controller 1575 obtains image data which is generated by the CPU 1505 or the like on a frame buffer provided within the RAM 1520, and causes the display device 1580 to display the obtained image data. Alternatively, the graphic controller 1575 may include therein a frame buffer for storing thereon the image data generated by the CPU 1505 or the like.

The I/O controller 1584 connects, to the host controller 1582, the hard disk drive 1540, communication interface 1530 and CD-ROM drive 1560 which are I/O devices operating at a relatively high rate. The communication interface 1530 communicates with different apparatuses via the network. The hard disk drive 1540 stores thereon programs and data to be used by the CPU 1505 in the image processing system 10. The CD-ROM drive 1560 reads programs or data from a CD-ROM 1595, and supplies the read programs or data to the hard disk drive 1540 via the RAM 1520.

The I/O controller 1584 is also connected to the ROM 1510, flexible disk drive 1550 and I/O chip 1570 which are I/O devices operating at a relatively low rate. The ROM 1510 stores thereon a boot program executed by the image processing system 10 at the startup, programs dependent on the hardware of the image processing system 10, and the like. The flexible disk drive 1550 reads programs or data from a flexible disk 1590, and supplies the read programs or data to the hard disk drive 1540 via the RAM 1520. The I/O chip 1570 is connected to the flexible disk drive 1550, and used to connect a variety of I/O devices to the image processing system 10, via a parallel port, a serial port, a keyboard port, a mouse port or the like.

The communication programs to be provided to the hard disk drive 1540 via the RAM 1520 are provided by a user in the state of being stored on a recording medium such as the flexible disk 1590, the CD-ROM 1595, and an IC card. The communication programs are read from the recording medium, and the read programs are installed in the hard disk drive 1540 in the image processing system 10 via the RAM 1520, to be executed by the CPU 1505. The communication programs that are installed in the image processing system 10 and executed cause the CPU 1505 and the like to cause the image processing system 10 to function as the respective constituents included in the image processing system 10 described with reference to FIGS. 1 to 12. For example, the programs cause the image processing system 10 to function as the image capturing section 110, the image processing section 140, the output section 180, the light irradiating section 150, the control section 105 and the like described with reference to FIGS. 1 to 12.

Although some aspects of the present invention have been described by way of exemplary embodiments, it should be understood that those skilled in the art might make many changes and substitutions without departing from the spirit and the scope of the present invention which is defined only by the appended claims.

What is claimed is:

1. An image processing system comprising:
   an object image obtaining section that obtains an object image formed by light from an object inside a physical body;
   a depth identifying section that identifies a depth from a surface of the physical body to the object;
   a distance information identifying section that identifies distance information indicating a distance from an image capturing section capturing the object image to the surface of the physical body; and
   an object image correcting section that corrects the object image according to the distance information and the depth.

2. The image processing system as set forth in claim 1, wherein
   the object image correcting section corrects spread of the object image according to the distance information and the depth.

3. The image processing system as set forth in claim 2, wherein
   the object image correcting section corrects the spread of the object image that occurs because the light from the object is scattered between the object and the surface, according to the distance information and the depth.

4. The image processing system as set forth in claim 2, further comprising
   a correction table that stores a correction value used to correct the spread of the object image, in association with the depth from the surface to the object, wherein
   the object image correcting section corrects the spread of the object image with reference to the distance information, the depth identified by the depth identifying section and the correction value.

5. The image processing system as set forth in claim 4, wherein
   the correction table stores the correction value in a real space in association with the depth from the surface to the object, and
   the object image correcting section includes:
   a correction value transforming section that transforms the correction value in a real space into a correction value in the object image, according to the distance information; and
   an object image correction section that corrects the spread of the object image by using the correction value in the object image produced by the correction value transforming section.

6. The image processing system as set forth in claim 2, wherein
   the object image correcting section increases the correction on the spread of the object image as the depth increases.

7. The image processing system as set forth in claim 2, wherein
   the object image correcting section increases the correction on the spread of the object image as the distance indicated by the distance information decreases.

8. The image processing system as set forth in claim 2, further comprising
   a light image obtaining section that obtains a plurality of light images each of which is captured by using light, from the object, in one of a plurality of different wavelength ranges, wherein
   the depth identifying section identifies the depth with reference to what is shown in the plurality of light images.

9. The image processing system as set forth in claim 8, further comprising
   an object region identifying section that identifies an image region of the object in each of the plurality of light images, wherein the depth identifying section identifies the depth with reference to luminance in the image region identified by the object region identifying section.

10. The image processing system as set forth in claim 8, wherein
the light image obtaining section obtains the plurality of light images by using light rays belonging to a plurality of different wavelength ranges including a light ray emitted from a luminescence substance inside the object.

11. The image processing system as set forth in claim 10, further comprising
a display control section that controls how to display the object image corrected by the object image correcting section, according to the depth.

12. The image processing system as set forth in claim 11, wherein
the display control section changes brightness or a color of the object image corrected by the object image correcting section, according to the depth.

13. The image processing system as set forth in claim 8, wherein
the light image obtaining section obtains the plurality of light images by using light reflected by the object.

14. The image processing system as set forth in claim 13, wherein
the light image obtaining section obtains the plurality of light images by using light rays belonging to a plurality of different wavelength ranges included in light reflected from the object when the object is irradiated with white light.

15. The image processing system as set forth in claim 13, wherein
the light image obtaining section obtains the plurality of light images by using light rays reflected from the object when the object is irradiated with light rays belonging to a plurality of different wavelength ranges.

16. The image processing system as set forth in claim 1, further comprising
a surface image obtaining section that obtains an image including a surface image that shows the surface of the physical body and is formed by light irradiated to the surface of the physical body in a direction substantially parallel to an image capturing direction of the image capturing section, wherein
the distance information identifying section identifies the distance information with reference to a size of the surface image included in the image obtained by the surface image obtaining section.

17. An image processing method comprising:
obtaining an object image formed by light from an object inside a physical body;
identifying a depth from a surface of the physical body to the object;
identifying distance information indicating a distance from an image capturing section capturing the object image to the surface of the physical body; and
correcting the object image according to the distance information and the depth.

18. A non-transitory computer readable medium including a program for use with an image processing system, execution of the program causing the image processing system to function as:
an object image obtaining section that obtains an object image formed by light from an object inside a physical body;
a depth identifying section that identifies a depth from a surface of the physical body to the object;
a distance information identifying section that identifies distance information indicating a distance from an image capturing section capturing the object image to the surface of the physical body; and
an image correcting section that corrects the object image according to the distance information and the depth.

* * * * *